United States Patent
Teles et al.

(10) Patent No.: US 10,544,116 B2
(45) Date of Patent: Jan. 28, 2020

(54) PROCESS FOR PURIFYING PROPYLENE OXIDE

(71) Applicant: BASF SE, Ludwigshafen am Rhein (DE)

(72) Inventors: Joaquim Henrique Teles, Ludwigshafen (DE); Marvin Kramp, Ludwigshafen (DE); Christian Mueller, Ludwigshafen (DE); Nicolai Tonio Woerz, Ludwigshafen (DE); Bernd Metzen, Ludwigshafen (DE); Tobias Keller, Ludwigshafen (DE); Dominic Riedel, Ludwigshafen (DE); Markus Weber, Ludwigshafen (DE); Daniel Urbanczyk, Ludwigshafen (DE); Andrei-Nicolae Parvulescu, Ludwigshafen (DE); Ulrike Wegerle, Worms (DE); Ulrich Mueller, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/315,680

(22) PCT Filed: Jul. 19, 2017

(86) PCT No.: PCT/EP2017/068228
§ 371 (c)(1),
(2) Date: Jan. 7, 2019

(87) PCT Pub. No.: WO2018/015435
PCT Pub. Date: Jan. 25, 2018

(65) Prior Publication Data
US 2019/0210989 A1  Jul. 11, 2019

(30) Foreign Application Priority Data
Jul. 20, 2016 (EP) .................................. 16180317

(51) Int. Cl.
| | | |
|---|---|---|
| C07D 301/12 | (2006.01) | |
| C07D 301/32 | (2006.01) | |
| C07D 303/04 | (2006.01) | |

(52) U.S. Cl.
CPC ......... C07D 301/32 (2013.01); C07D 301/12 (2013.01); C07D 303/04 (2013.01)

(58) Field of Classification Search
CPC ... C07D 301/12; C07D 301/32; C07D 303/04
(Continued)

(56) References Cited

U.S. PATENT DOCUMENTS

| | | |
|---|---|---|
| 4,369,096 A | 1/1983 | Seifert et al. |
| 5,133,839 A | 7/1992 | Shih |

(Continued)

FOREIGN PATENT DOCUMENTS

| | | |
|---|---|---|
| EP | 0 004 019 A2 | 9/1979 |
| EP | 0 675 119 A2 | 10/1995 |

(Continued)

OTHER PUBLICATIONS

U.S. Appl. No. 15/509,238, filed Mar. 7, 2017, US 2017/0283352 A1, Thomas Fenlon, et al.

(Continued)

*Primary Examiner* — Taylor V Oh
(74) *Attorney, Agent, or Firm* — Oblon, McClelland, Maier & Neustadt, L.L.P.

(57) ABSTRACT

Disclosed herein is a process for purifying propylene oxide, including the steps of: (i) providing a stream S0 containing propylene oxide, acetonitrile, water, and an organic compound containing a carbonyl group —C(=O)—; and (ii) separating propylene oxide from the stream S0 by subjecting the stream S0 to distillation conditions in a distillation column to obtain a gaseous top stream S1c which is enriched in propylene oxide compared to the stream S0, a liquid (Continued)

bottoms stream S1a which is enriched in acetonitrile and water compared to the stream S0, and a side stream S1b containing propylene oxide which is enriched in the carbonyl compound compared to the stream S0.

20 Claims, 1 Drawing Sheet

(58) Field of Classification Search
USPC .......................................................... 549/531
See application file for complete search history.

(56) References Cited

U.S. PATENT DOCUMENTS

| | | | |
|---|---|---|---|
| 5,489,366 | A | 2/1996 | Jongenburger |
| 6,339,194 | B1 | 1/2002 | Larsen et al. |
| 9,458,080 | B2 | 10/2016 | Woerz et al. |
| 9,546,123 | B2 | 1/2017 | Brueggemann et al. |
| 9,593,065 | B2 | 3/2017 | Schulz et al. |
| 9,695,099 | B2 | 7/2017 | Liu et al. |
| 9,738,583 | B2 | 8/2017 | Hartmann et al. |
| 9,771,314 | B2 | 9/2017 | Hartmann et al. |
| 9,969,708 | B2 | 5/2018 | Vautravers et al. |
| 10,087,395 | B2 | 10/2018 | Pelzer et al. |
| 10,112,882 | B2 | 10/2018 | Thrun et al. |
| 10,144,691 | B2 | 12/2018 | Vautravers et al. |
| 10,195,598 | B2 | 2/2019 | Riedel et al. |
| 10,196,276 | B2 | 2/2019 | Maurer et al. |
| 10,202,323 | B2 | 2/2019 | Parvulescu et al. |
| 10,202,324 | B2 | 2/2019 | Vautravers et al. |
| 2004/0106811 | A1 | 6/2004 | Hofen et al. |
| 2016/0115140 | A1 | 4/2016 | Teles et al. |
| 2016/0362387 | A1 | 12/2016 | Teles et al. |

FOREIGN PATENT DOCUMENTS

| | | |
|---|---|---|
| EP | 1 122 249 A1 | 8/2001 |
| EP | 2 173 731 A2 | 4/2010 |
| JP | 44-9650 A | 5/1969 |
| WO | WO 2004/048355 A1 | 6/2004 |
| WO | WO 2014/177507 A1 | 11/2014 |
| WO | WO 2016/066629 A1 | 5/2016 |

OTHER PUBLICATIONS

U.S. Appl. No. 15/509,228, filed Mar. 7, 2017, US 2017/0275225 A1, Dominic Riedel, et al.
U.S. Appl. No. 15/509,527, filed Mar. 8, 2017, US 2017/0246620 A1, Andrei-Nicolae Parvulescu, et al.
U.S. Appl. No. 15/683,905, filed Aug. 23, 2017, US 2017/0368541 A1, Natalia Trukhan, et al.
U.S. Appl. No. 15/549,905, filed Aug. 9, 2017, US 2018/0022611 A1, Mathias Feyen, et al.
U.S. Appl. No. 15/752,991, filed Feb. 15, 2018, US 2018/0243691 A1, Ulrich Mueller, et al.
U.S. Appl. No. 15/518,945, filed Apr. 13, 2017, US 2017/0225959 A1, Stefan Maurer, et al.
U.S. Appl. No. 15/524,484, filed May 4, 2017, US 2017/0336030 A1, Matthias Weickert, et al.
U.S. Appl. No. 15/779,218, filed May 25, 2018, US 2018/0345245 A1, Stefan Maurer, et al.
U.S. Appl. No. 15/777,931, filed May 22, 2018, US 2018/0346478 A1, Albert Werner, et al.
U.S. Appl. No. 15/508,725, filed Mar. 3, 2017, US 2017/0275076 A1, Todd Edgington, et al.
U.S. Appl. No. 15/521,924, filed Apr. 26, 2017, US 2018/0230117 A1, Joaquim Henrique Teles, et al.
U.S. Appl. No. 15/744,474, filed Jan. 12, 2018, US 2018/0208533 A1, Stefan Rüdenauer, et al.
U.S. Appl. No. 16/086,251, filed Sep. 18, 2018, Benedikt Kalo.
U.S. Appl. No. 15/746,183, filed Jan. 19, 2018, US 2018/0208745 A1, Nicolas Vautravers, et al.
U.S. Appl. No. 15/779,314, filed May 25, 2018, US 2018/0333696 A1, Julia Burckhart, et al.
U.S. Appl. No. 15/746,082, filed Jan. 19, 2018, US 2018/0215724 A1, Alvaro Gordillo, et al.
U.S. Appl. No. 16/060,260, filed Jun. 7, 2018, US 2018/0362353 A1, Nicolas Vautravers, et al.
U.S. Appl. No. 16/076,600, filed Aug. 8, 2018, Dominic Riedel, et al.
U.S. Appl. No. 15/766,425, filed Apr. 6, 2018, US 2018/0312458 A1, Frauke Thrun, et al.
U.S. Appl. No. 15/766,407, filed Apr. 6, 2018, US 2018/0290959 A1, Frauke Thrun, et al.
U.S. Appl. No. 16/308,730, filed Dec. 10, 2018, Natalia Trukhan, et al.
U.S. Appl. No. 15/775,657, filed May 11, 2018, US 2018/0328601 A1, Matthias Weickert, et al.
U.S. Appl. No. 16/060,739, filed Jun. 8, 2018, US 2018/0362357 A1, Mathias Feyen, et al.
U.S. Appl. No. 16/318,221, filed Jan. 16, 2019, Joaquim Henrique Teles, et al.
U.S. Appl. No. 16/060,229, filed Jun. 7, 2018, US 2018/0362351 A1, Andrei Nicolae Parvulescu, et al.
U.S. Appl. No. 16/315,345, filed Jan. 4, 2019, Joaquim Henrique Teles, et al.
U.S. Appl. No. 15/348,217, filed Nov. 10, 2016, US 2017/0128916 A1, Michael Lejkowski, et al.
U.S. Appl. No. 16/073,941, filed Jul. 30, 2018, US 2019/0040005 A1, Richard Dehn, et al.
U.S. Appl. No. 16/310,645, filed Dec. 17, 2018, Andrei-Nicolae Parvulescu, et al.
U.S. Appl. No. 16/304,511, filed Nov. 26, 2018, Mathias Feyen, et al.
U.S. Appl. No. 16/307,450, filed Dec. 5, 2018, Min-che Chen, et al.
U.S. Appl. No. 16/308,928, filed Dec. 11, 2018, Stefan Marx, et al.
International Search Report and Written Opinion of the International Searching Authority dated Oct. 11, 2017 in PCT/EP2017/068228 filed Jul. 19, 2017, citing documents AA-AE, AO-AS and AY therein, 12 pages.
International Preliminary Report on Patentability dated Jan. 31, 2019 in PCT/EP2017/068228 filed Jul. 19, 2017, citing documents AO-AS therein, 7 pages.
"Hydrogen Peroxide" Ullmann's Encyclopedia of Industrial chemistry, 5$^{th}$ Edition, vol. A13, 1989, pp. 443-466.

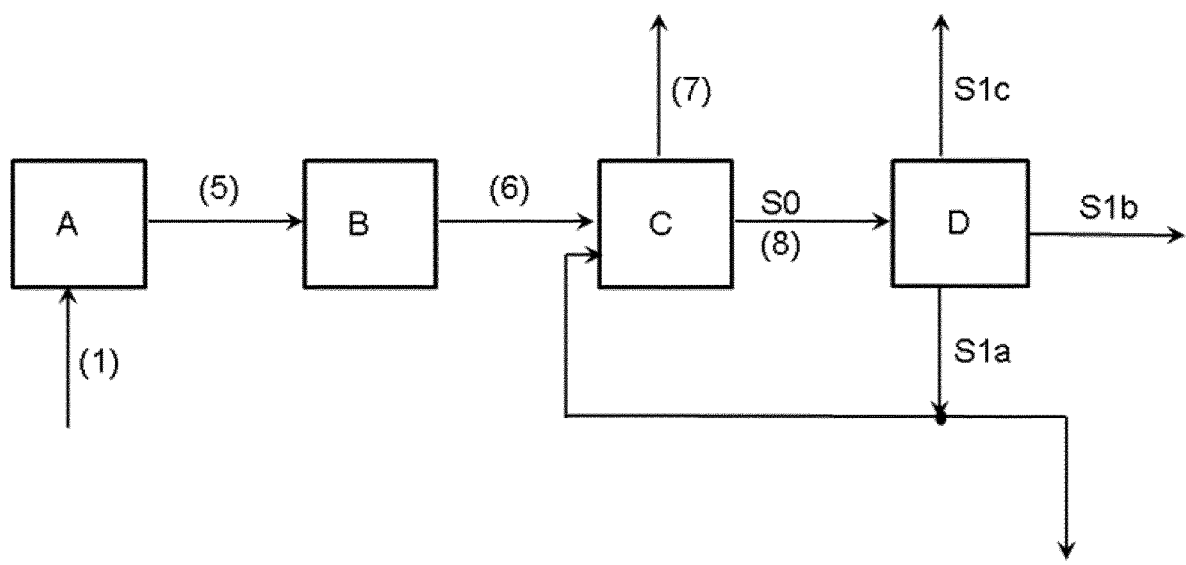

PROCESS FOR PURIFYING PROPYLENE OXIDE

The present invention is directed to a process for purifying propylene oxide, wherein propylene oxide is separated from a stream comprising propylene oxide, acetonitrile, water, and an organic compound comprising a carbonyl group —C(=O)—, which comprises one or more of acetone and propionaldehyde, by distillation in a distillation column, wherein a side stream comprising propylene oxide, which is enriched in the carbonyl compound, is taken off; wherein the distillation column is operated at an absolute pressure at the top of the distillation column in the range of from 0.1 to 2.0 bar and an internal reflux ratio in the range of from 2.0 to 6.0; and wherein the distillation column exhibits at least 100 theoretical trays, the rectifying section of the distillation column consists of from 30 to 70% of the theoretical trays and the stripping section of the distillation column consists of from 70 to 30% of the theoretical trays.

Propylene oxide is an important intermediate in the chemical industry. A suitable process for the preparation of propylene oxide starts from propene and makes use of hydrogen peroxide as oxidizing agent, acetonitrile as solvent and an epoxidation catalyst comprising a titanium zeolite. Due to its importance for industrial-scale processes, it is desired to carry out the epoxidation reaction as efficiently as possible and to purify the propylene oxide efficiently and to a high degree. The epoxidation reaction results in a mixture comprising acetonitrile, water, propylene oxide and side products, for example, organic compound comprising a carbonyl group —C(=O)— such as acetone, propionaldehyde. Especially these compounds such as acetone, propionaldehyde, which have a boiling point higher than the boiling point of propylene oxide and lower than the boiling point of the azeotropic mixture of acetonitrile and water, are challenging when it comes to separating them from the propylene oxide.

U.S. Pat. No. 5,133,839 A discloses the removal of propionaldehyde and acetone from propylene oxide using at least four distillation columns. U.S. Pat. No. 5,489,366 A also describes the removal of propionaldehyde and acetone from propylene oxide in an extractive distillation using an extractive distillation solvent and a plurality of destillative columns.

JP 44009650 A discloses the removal of carbonyl compounds, especially propionaldehyde by contacting crude propylene oxide with hydrazine hydrate and distillation. The method requires hydrazine in stoichiometric amounts in relation to the carbonyl compounds which are to be removed.

U.S. Pat. No. 4,369,096 A describes the removal of carbonyl compounds from propylene oxide by use of hydrazine containing solutions in the propylene oxide distillation. Only one distillation column is required starting from a propylene oxide/solvent mixture in order to arrive at pure propylene oxide. However, the method requires the use of hydroxylamine in stoichiometric amounts in relation to the components which are to be removed. The method is only described for solvents such as ethylbenzene, methyl phenyl carbinol, benzene, toluene, acetic acid, tert-butanol, water, dichloropropane or mixtures thereof, wherein all these solvents are easily separable from propylene oxide by distillation.

WO 2004/048355 A discloses a method using methanol as solvent, which is less easy separable from propylene by distillation.

EP 2 173 731 A2 describes the preparation of propylene oxide by epoxidation of propene with hydrogen peroxide in acetonitrile and with a TiMWW catalyst, as well as the destillative purification of propylene oxide. However, the document is silent whether propionaldehyde or acetone are formed as side products and thus does not disclose means to remove these carbonyl compounds.

It was an object of the present invention to provide a process for the purification of propylene oxide which is efficient, economically advantageous, does not require additives such as hydrazine and allows to essentially remove carbonyl compounds from a propylene oxide stream.

Surprisingly, it was found that for the separation of carbonyl compounds from propylene oxide, i.e. for the purification of propylene oxide, disadvantages can be avoided by taking of a side stream from a propylene oxide distillation, wherein the side stream comprises propylene oxide and is enriched in the carbonyl compound, if only one distillation unit is used and operated at specific parameters. For the carbonyl compounds which were found to be critical, it was surprisingly found that they could be separated selectively and very efficiently from the gaseous propylene oxide top stream of the distillation unit, without causing a pollution of the liquid bottoms stream from the distillation unit, which is enriched in acetonitrile and water, with carbonyl compounds. Surprisingly, no additives such as hydrazine were needed and also the loss on propylene oxide could be kept very low. Yet further, it was found that—besides a significant reduction of the carbonyl compound content—also the water content of the gaseous propylene oxide top stream could be reduced significantly.

Therefore, the present invention relates to a process for purifying propylene oxide, comprising
(i) providing a stream S0 comprising propylene oxide, acetonitrile, water, and an organic compound comprising a carbonyl group —C(=O)—, wherein said organic compound comprising a carbonyl group —C(=O)— (carbonyl compound) comprises one or more of acetone and propionaldehyde;
(ii) separating propylene oxide from the stream S0 by distillation, comprising subjecting the stream S0 to distillation conditions in a distillation column, obtaining a gaseous top stream S1c which is enriched in propylene oxide compared to the stream S0, a liquid bottoms stream S1a which is enriched in acetonitrile and water compared to the stream S0, and a side stream S1b comprising propylene oxide which is enriched in the carbonyl compound compared to the stream S0;
wherein the distillation column is operated at an absolute pressure at the top of the distillation column in the range of from 0.1 to 2.0 bar and an internal reflux ratio in the range of from 2.0 to 6.0;
wherein the distillation column exhibits at least 100 theoretical trays, the rectifying section of the distillation column consists of from 30 to 70%, preferably of from 40 to 60%, of the theoretical trays and the stripping section of the distillation column consists of from 70 to 30%, preferably of from 60 to 40%; of the theoretical trays.

Preferred Parameters of the Distillation Column

Preferably, the distillation column is operated at an absolute pressure at the top of the distillation column in the range of from 0.2 to 1.5 bar, more preferably in the range of from 0.3 to 1.0 bar, more preferably in the range of from 0.45 to 0.55 bar.

Preferably, the distillation column is operated at a reflux ratio in the range of from 2.5 to 5.5, more preferably in the range of from 3.0 to 5.0, more preferably in the range of from 3.5 to 4.5.

Preferably, the distillation column exhibits from 100 to 150, preferably from 105 to 145, more preferably from 110 to 140, more preferably from 115 to 135, more preferably from 120 to 130 theoretical trays.

Preferably, the distillation column is operated at an absolute pressure at the top of the column in the range of from 0.45 to 0.55 bar and a reflux ratio in the range of from 3.5 to 4.5, and wherein the distillation column exhibits from 120 to 130 theoretical trays.

Therefore, the present invention also relates to a process for purifying propylene oxide, comprising
(i) providing a stream S0 comprising propylene oxide, acetonitrile, water, and an organic compound comprising a carbonyl group —C(=O)—, wherein said organic compound comprising a carbonyl group —C(=O)— comprises one or more of acetone and propionaldehyde;
(ii) separating propylene oxide from the stream S0 by distillation, comprising subjecting the stream S0 to distillation conditions in a distillation column, obtaining a gaseous top stream S1c which is enriched in propylene oxide compared to the stream S0, a liquid bottoms stream S1a which is enriched in acetonitrile and water compared to the stream S0, and a side stream S1b comprising propylene oxide which is enriched in the carbonyl compound compared to the stream S0;
wherein the distillation column is operated at an absolute pressure at the top of the column in the range of from 0.45 to 0.55 bar and a reflux ratio in the range of from 3.5 to 4.5;
wherein the distillation column exhibits from 120 to 130 theoretical trays, the rectifying section of the distillation column consists of from 40 to 60% of the theoretical trays and the stripping section of the distillation column consists of from 60 to 40% of the theoretical trays.

Stream S0

According to (i), a stream S0 is provided comprising propylene oxide, acetonitrile, water, and an organic compound comprising a carbonyl group —C(=O)—, wherein said organic compound comprising a carbonyl group —C(=O)— comprises one or more of acetone and propionaldehyde.

Preferably, the organic compound comprising a carbonyl group —C(=O)— is a reaction product from the epoxidation of propylene with hydrogen peroxide or with a source of hydrogen peroxide. Generally, there are no specific restrictions what further organic compound comprising a carbonyl group —C(=O)— is comprised besides one or more of acetone and propionaldehyde. Preferably, the organic compound comprising a carbonyl group —C(=O)— further comprises, i.e. in addition to one or more of acetone and propionaldehyde, one or more further aldehydes, one or more further ketones, or a mixture of one or more further aldehydes and one or more further ketones.

More preferably, the organic compound comprising a carbonyl group —C(=O)— further comprises, i.e. in addition to one or more of acetone and propionaldehyde, one or more of acetaldehyde, formaldehyde, butyraldehyde, isobutyraldehyde, 2-butanon, 1-pentanal, 2-pentanon, 3-pentanon, 2-methylpentanone, preferably one or more of acetaldehyde, formaldehyde, butyraldehyde, isobutyraldehyde, more preferably at least acetaldehyde.

Generally, the composition of the stream S0 provided in (i) is not subject to any specific restrictions. Preferably, at least 95 weight-%, more preferably at least 98 weight-%, more preferably at least 99 weight-% of the stream S0 consist of propylene oxide, acetonitrile, water, and the organic compound comprising a carbonyl group. Preferably, the stream S0 comprises the propylene oxide in amount of from 5 to 15 weight-%, more preferably from 8 to 12 weight-%, based on the total weight of the stream S0; the acetonitrile in an amount of from 60 to 80 weight-%, preferably from 65 to 75 weight-%, based on the total weight of the stream S0; the water in amount of from 10 to 25 weight-%, preferably from 17 to 21 weight-%, based on the total weight of the stream S0; propionaldehyde in an amount of from 100 to 300 weight-ppm, preferably from 150 to 250 weight-ppm, based on the total weight of the stream S0; acetone in an amount of from 60 to 200 weight-ppm, preferably from 80 to 120 weight-ppm, based on the total weight of the stream S0; and acetaldehyde in an amount of from 80 to 300 weight-ppm, preferably from 100 to 200 weight-ppm, based on the total weight of the stream S0.

Side Stream S1b

According to (ii) the stream S0 is subjected to distillation conditions in a distillation column and a side stream S1b comprising propylene oxide, which is enriched in the carbonyl compound compared to the stream S0, is obtained. Generally, there are no specific restrictions regarding the point where the side stream S1b is taken off from the distillation column provided that side stream S1b comprises propylene oxide and is enriched in the carbonyl compound compared to the stream S0. Preferably, the side stream S1b is removed from the rectifying section of the distillation column. More preferably, the side stream S1b is removed from the rectifying section of the distillation column at a position which is at least 1 theoretical tray above the stripping section of the distillation column. Preferably, the side stream S1b is removed from the rectifying section of the distillation column at a position which is from 1 to 20, more preferably from 2 to 19, more preferably from 3 to 18, more preferably from 4 to 17, more preferably from 5 to 16, more preferably from 5 to 15 theoretical tray above the stripping section of the distillation column.

Generally, no restrictions exists regarding the composition of the side stream S1b provided that it comprises propylene oxide and is enriched in the carbonyl compound compared to the stream S0. Said organic compound comprising a carbonyl group —C(=O)— comprises one or more of acetone and propionaldehyde. In other words, side stream S1b comprises propylene oxide and is enriched in the carbonyl compound, which comprises one or more of acetone and propionaldehyde. Preferably, the side stream S1b comprises the organic compound comprising a carbonyl group in an amount of ≥10 weight-%, more preferably ≥15 weight-%; based on the total weight of the side stream S1 b; wherein the organic compound comprising a carbonyl group preferably comprises propionaldehyde in an amount of ≥10 weight-% based on the total weight of the side stream S1b and acetone in an amount of ≥5 weight-% based on the total weight of the side stream S1 b. Preferably, at least 95 weight-%, more preferably at least 98 weight-%, more preferably at least 99 weight-% of the side stream S1b consist of propylene oxide, acetonitrile, water, and the organic compound comprising a carbonyl group.

Preferably, the side stream S1b comprises the propylene oxide in an amount of from 60 to 80 weight-%, more preferably from 65 to 75 weight-%, based on the total weight of the side stream S1 b; the acetonitrile in an amount of from 2 to 6 weight-%, preferably from 3.5 to 5.5 weight-%, based on the total weight of the side stream S1 b; the organic compound comprising a carbonyl group in an amount of from 10 to 30 weight-%, preferably from 15 to 25 weight-%; based on the total weight of the side stream S1 b; wherein the organic compound comprising a carbonyl group preferably comprises propionaldehyde in an amount of from 10 to 20 weight-%, preferably from 12 to 16 weight-%, based on the total weight of the side stream S1 b, and acetone in an amount of from 5 to 10 weight-%, preferably from 5 to 9 weight-%, based on the total weight of the side stream S1 b.

Preferably, the organic compound comprising a carbonyl group —C(=O)— comprises further, i.e. in addition to one or more of acetone and propionaldehyde, one or more further aldehydes, one or more further ketones, or a mixture of one or more further aldehydes and one or more further ketones. In other words, the stream S1b is further enriched, i.e. in addition to being enriched in one or more of acetone and propionaldehyde, in one or more further aldehydes, one or more further ketones, or a mixture of one or more further aldehydes and one or more further ketones. More preferably, the side stream S1b obtained in (ii) comprising propylene oxide and being enriched in the carbonyl compound compared to the stream S0 is further enriched, i.e. in addition to being enriched in one or more of acetone and propionaldehyde, in one or more of acetaldehyde, formaldehyde, butyraldehyde, isobutyraldehyde, 2-butanon, 1-pentanal, 2-pentanon, 3-pentanon, 2-methylpentanone, preferably one ore more of acetaldehyde, formaldehyde, butyraldehyde, isobutyraldehyde, more preferably at least in acetaldehyde.

Stream S1c

According to (ii), a gaseous top stream S1c is obtained, which is enriched in propylene oxide compared to the stream S0. Preferably, the top stream S1c obtained in (ii) contains at least 99.00 weight-%, more preferably at least 99.50 weight-%, more preferably at least 99.80 weight-%, propylene oxide based on the total weight of the stream S1c. Preferably, the top stream S1c obtained in (ii) contains at the outmost 50 weight-ppm, more preferably at the outmost 25 weight-ppm, more preferably at the outmost 20 weight-ppm of the organic compound comprising a carbonyl group based on the total weight of the stream S1c.

Preferably, the top stream S1c obtained in (ii) contains less than 20 weight-ppm, more preferably less than 15 weight-ppm, propionaldehyde based on the total weight of the stream S1c.

Preferably, the top stream S1c obtained in (ii) contains at the outmost 100 weight-ppm, more preferably at the outmost 75 weight-ppm, more preferably at the outmost 50 weight-ppm water based on the total weight of the stream S1c.

Therefore, in one preferred embodiment, a top stream S1c is obtained in (ii), which contains at the outmost 100 weight-ppm, preferably at the outmost 75 weight-ppm, more preferably at the outmost 50 weight-ppm water based on the total weight of the stream S1c and which contains less than 20 weight-ppm, preferably less than 15 weight-ppm, propionaldehyde based on the total weight of the stream S1c.

Preferably, the top stream S1c obtained in (ii) contains less than 10 weight-ppm, more preferably less than 5 weight-ppm acetone based on the total weight of the stream S1c.

Preferably, the top stream S1c obtained in (ii) comprises the propylene oxide in an amount of at least 99.00 weight-%, more preferably at least 99.50 weight-%, more preferably at least 99.80 weight-%, propylene oxide, based on the total weight of the stream S1c; the organic compound comprising a carbonyl group in an amount of at the outmost 50 weight-ppm, preferably at the outmost 25 weight-ppm, more preferably at the outmost 20 weight-ppm, based on the total weight of the stream S1c; and water in an amount of at the outmost 100 weight-ppm, preferably at the outmost 75 weight-ppm, more preferably at the outmost 50 weight-ppm, based on the total weight of the stream S1c. More preferably, the top stream S1c obtained in (ii) comprises the propylene oxide in an amount of at least 99.00 weight-%, more preferably at least 99.50 weight-%, more preferably at least 99.80 weight-%, propylene oxide, based on the total weight of the stream S1c; propionaldehyde in an amount of less than 20 weight-ppm, more preferably less than 15 weight-ppm, based on the total weight of the stream S1c; acetone in an amount of less than 10 weight-ppm, more preferably less than 5 weight-ppm, based on the total weight of the stream S1c; and water in an amount of at the outmost 100 weight-ppm, more preferably at the outmost 75 weight-ppm, more preferably at the outmost 50 weight-ppm, based on the total weight of the stream S1c.

Stream S1a

According to (ii), a liquid bottoms stream S1a, which is enriched in acetonitrile and water compared to the stream S0, is obtained. Preferably, bottoms stream S1a contains the organic compound comprising a carbonyl group in an amount of at most 20 weight-ppm, more preferably at most 10 weight-ppm, more preferably at most 2 weight-ppm, based on the weight of S1a. Preferably, bottoms stream S1a contains propionaldehyde in an amount of at most 10 weight-ppm, more preferably at most 5 weight-ppm, more preferably at most 1 weight-ppm, based on the weight of S1a. Preferably, bottoms stream S1a contains acetone in an amount of at most 10 weight-ppm, more preferably at most 5 weight-ppm, more preferably at most 1 weight-ppm, based on the weight of S1a.

Preferably, at least 95 weight-% of bottoms stream S1a consist of acetonitrile and water, wherein preferably, the weight ratio of acetonitrile relative to water in the stream S1a is greater than 1:1. Preferably, bottoms stream S1a contains at most 10 weight-ppm, preferably at most 5 weight-ppm, more preferably at most 1 weight-ppm, of the propylene oxide, based on the weight of S1a.

More preferably, bottoms stream S1a comprises the acetonitrile in an amount of from 70 to 80 weight-%, based on the weight of S1a; water in an amount of from 10 to 30 weight-% based on the weight of stream S1a; at most 10 weight-ppm, more preferably at most 5 weight-ppm, more preferably at most 1 weight-ppm, of the propylene oxide, based on the weight of stream S1a; and each of propionaldehyde and acetone in an amount of at most 10 weight-ppm, preferably at most 5 weight-ppm, more preferably at most 1 weight-ppm, based on the weight of stream S1a.

Generally, the stream S1a as described above can be used as acetonitrile recycle stream which can be used for providing the liquid feed stream in (a) (described herein later below). Further, it is possible that the stream S1a is subjected to further work-up steps before it is used as acetonitrile recycle stream which is used for providing the liquid feed stream in (a). Preferably, a part of S1a is introduced to the distillation unit employed for the separation in (d) (described herein later below) as extracting agent, preferably in the upper part of the distillation unit.

Preferably, the process for purifying propylene oxide according to the present invention is a continuous process.

Origin of stream S0

Generally, no restrictions exist from where the stream S0 originates and it can be provided in (i) according to any conceivable method. In one preferred embodiment of the present invention, the stream S0 is obtainable or obtained by a, preferably continuous, process comprising
  (a) providing a stream comprising propene and preferably propane, hydrogen peroxide or a source of hydrogen peroxide, water, and acetonitrile;
  (b) passing the liquid feed stream provided in (a) into an epoxidation zone comprising an epoxidation catalyst comprising a titanium zeolite, and subjecting the liquid feed stream to epoxidation reaction conditions in the epoxidation zone, obtaining a reaction mixture comprising propene and preferably propane, propylene oxide, water, acetonitrile, and the organic compound comprising a carbonyl group;
  (c) removing an effluent stream from the epoxidation zone, the effluent stream comprising propylene oxide, water, acetonitrile, propene and preferably propane, and the organic compound comprising a carbonyl group;
  (d) separating propene and preferably propane from the effluent stream by distillation, comprising subjecting the effluent stream to distillation conditions in a distillation unit, obtaining a gaseous stream which is enriched in propene and preferably propane compared to the effluent stream subjected to distillation conditions, and a liquid bottoms stream which is enriched in propylene oxide, water, acetonitrile and the organic compound comprising a carbonyl group compared to the effluent stream subjected to distillation conditions;
  wherein said liquid bottoms stream obtained according to (d) is the stream S0.

In another preferred embodiment of the present invention providing the stream S0 according to (i) comprises
  (a) providing a stream comprising propene and preferably propane, hydrogen peroxide or a source of hydrogen peroxide, water, and acetonitrile;
  (b) passing the liquid feed stream provided in (a) into an epoxidation zone comprising an epoxidation catalyst comprising a titanium zeolite, and subjecting the liquid feed stream to epoxidation reaction conditions in the epoxidation zone, obtaining a reaction mixture comprising propene and preferably propane, propylene oxide, water, acetonitrile, and the organic compound comprising a carbonyl group;
  (c) removing an effluent stream from the epoxidation zone, the effluent stream comprising propylene oxide, water, acetonitrile, propene and preferably propane, and the organic compound comprising a carbonyl group;
  (d) separating propene and preferably propane from the effluent stream by distillation, comprising subjecting the effluent stream to distillation conditions in a distillation unit, obtaining a gaseous stream which is enriched in propene and preferably propane compared to the effluent stream subjected to distillation conditions, and a liquid bottoms stream which is enriched in propylene oxide, water, acetonitrile and and the organic compound comprising a carbonyl group compared to the effluent stream subjected to distillation conditions;
  wherein said liquid bottoms stream obtained according to (d) is the stream S0. The steps (a) to (d) are preferably done in a continuous manner.

Preferably, the effluent stream removed according to (c) further comprises oxygen, wherein (d) comprises separating oxygen, propene and preferably propane from the effluent stream by distillation, comprising subjecting the effluent stream to distillation conditions in a distillation unit, obtaining a gaseous stream which is enriched in oxygen, propene and preferably propane compared to the effluent stream subjected to distillation conditions, and a liquid bottoms stream which is enriched in propylene oxide, water and acetonitrile compared to the effluent stream subjected to distillation conditions.

Preferably, the effluent stream removed according to (c) is depressurized prior to (d), preferably to a pressure of from 0.5 to 2.8 bar, more preferably of from 0.6 to 2.5 bar, more preferably of from 0.8 to 1.5 bar. More preferably, a gaseous stream and a liquid stream are obtained from depressurizing the effluent stream, wherein more preferably the gaseous and liquid streams are passed separately to the distillation unit, preferably the distillation tower, employed according to (d), more preferably to different theoretical trays of the distillation tower employed according to (d).

Generally, the stream comprising propene and preferably propane, hydrogen peroxide or a source of hydrogen peroxide, water, and acetonitrile can be provided in (a) according to any conceivable method. Preferably, the stream is provided in (a) by combining at least three individual streams wherein a first stream comprises hydrogen peroxide or a source of hydrogen peroxide, a second stream comprises propene and preferably propane and a third stream comprises acetonitrile and optionally water.

Preferably, the stream comprising propene additionally comprises propane wherein preferably at least 98 weight-%, more preferably at least 99 weight-%, more preferably at least 99.5 weight-%, more preferably at least 99.9 weight-% of the stream consist of propene and propane. Preferably, the weight ratio of propene relative to propane in the stream is at least 7:3. For example, commercially available propene can be employed which may be either a polymer grade propene or a chemical grade propene. Typically, polymer grade propene has a propene content in the range of from 99 to 99.8 weight-% and a propane content in the range of from 0.2 to 1 weight-%. Chemical grade propene typically has a propene content in the range of from 92 to 98 weight-% and a propane content in the range of from 2 to 8 weight-%. Preferably, a stream is employed having a propene content in the range of from 99 to 99.8 weight-% and a propane content in the range of from 0.2 to 1 weight-%.

The stream comprising hydrogen peroxide can be prepared according to every conceivable method. It is conceivable to obtain the stream comprising hydrogen peroxide by converting sulphuric acid into peroxodisulphuric acid by anodic oxidation with simultaneous evolution of hydrogen at the cathode. Hydrolysis of the peroxodisulphuric acid then leads via peroxomonosulphuric acid to hydrogen peroxide and sulphuric acid which is thus obtained back. The preparation of hydrogen peroxide from the elements is also conceivable. Depending on the specific preparation method, the stream comprising hydrogen peroxide can be, for example, an aqueous or an aqueous/methanolic hydrogen peroxide stream, preferably an aqueous hydrogen peroxide stream. In case an aqueous hydrogen peroxide feed is employed, the content of the stream with respect to hydrogen peroxide is usually in the range of from 3 to 85 weight-%, preferably from 25 to 75 weight-%, more preferably from 30 to 50 weight-%, such as from 30 to 40 weight-% or from 35 to 45 weight-% of from 40 to 50 weight-%. Preferably, at least 25 weight-%, more preferably at least 30 weight-%, more preferably at least 35 weight-% of the stream comprising hydrogen peroxide consist of water and hydrogen peroxide. Preferred ranges are from 30 to 80 weight % or from 35 to 75 weight-% or from 40 to 70 weight-%.

According to the present invention, it is preferred to employ a stream comprising hydrogen peroxide which is obtained as crude hydrogen peroxide solution by extraction of a mixture which results from a process known as anthraquinone process by means of which virtually the entire world production of hydrogen peroxide is produced (see, e.g., Ullmann's Encyclopedia of Industrial Chemistry, 5th edition, volume A 13 (1989) pages 443-466) wherein a solution of an anthraquinone is used containing an alkyl group preferably having of from 2 to 10 carbon atoms, more preferably at least 5 carbon atoms such as 5 carbon atoms or 6 carbon atoms and where the solvent used usually consists of a mixture of two different solvents, wherein preferably none of the solvents is a nitrogen containing substance. This solution of the anthraquinone is usually referred to as the working solution. In this process, the hydrogen peroxide formed in the course of the anthraquinone process is generally separated by extraction from the respective working solution after a hydrogenation/re-oxidation cycle. Said extraction can be performed preferably with essentially pure water, and the crude aqueous hydrogen peroxide solution is obtained. While it is generally possible to further purify the thus obtained crude aqueous hydrogen peroxide solution by distillation, it is preferred, according to the present invention, to use such crude aqueous hydrogen peroxide solution which has not been subjected to purification by distillation. Further, it is generally possible to subject the crude aqueous hydrogen peroxide solution to a further extraction stage wherein a suitable extracting agent, preferably an organic solvent is used. More preferably, the organic solvent used for this further extraction stage is the same solvent which is used in the anthraquinone process. Preferably the extraction is performed using just one of the solvents in the working solution and most preferably using just the most nonpolar solvent of the working solution. In case the crude aqueous hydrogen peroxide solution is subjected to such further extraction stage, a so-called crude washed hydrogen peroxide solution is obtained. According to a preferred embodiment of the present invention, the crude washed hydrogen peroxide solution is used as hydrogen peroxide feed. The production of a crude solution is described, for example, in European patent application EP 1 122 249 A1. As to the term "essentially pure water", reference is made to paragraph 10, page 3 of EP 1 122 249 A1 which is incorporated by reference. The hydrogen peroxide can also be treated to remove trace metals, for example, as described in the WO 2015/049327 A1 before use.

It is conceivable that the hydrogen peroxide is prepared in situ in the epoxidation zone from hydrogen and oxygen, preferably in the presence of a suitable noble metal catalyst comprised in the epoxidation zone according to (b). A suitable noble metal catalyst preferably comprises one or more of palladium, platinum, silver, gold, rhodium, iridium, ruthenium and osmium. Preferably, the noble metal catalyst comprises palladium. The noble metal catalyst is preferably supported on a carrier, wherein the carrier preferably comprises one or more of $SiO_2$, $Al_2O_3$, $B_2O_3$, $GeO_2$, $Ga_2O_3$, $ZrO_2$, $TiO_2$, MgO, carbon and one or more zeolites, preferably one or more titanium zeolites. More preferably, the carrier comprises the epoxidation catalyst comprising a titanium zeolite. If hydrogen peroxide is prepared in the epoxidation zone according to (b) in situ from hydrogen and oxygen, the stream provided in (a) comprises propene and preferably propane, hydrogen, oxygen, water, and acetonitrile.

According to (b), the liquid feed stream provided in (a) is passed into an epoxidation zone. Generally, there are no specific restrictions regarding the design of the epoxidation zone provided that it is suitable for carrying out a, preferably continuous, epoxidation reaction. Preferably, the epoxidation zone according to (b) comprises one or more epoxidation subzone wherein a given epoxidation subzone preferably consist of one or more epoxidation reactors wherein, with regard to the design of the one or more epoxidation reactors, no specific restrictions exist provided that the reactors are suitable for carrying out a, preferably continuous, epoxidation reaction.

Preferably, the epoxidation zone according to (b) comprises a first epoxidation subzone consisting of one or more epoxidation reactors A. The term "first epoxidation subzone" as used in this context of the present invention relates to the epoxidation subzone into which the liquid feed stream provided in (a) is passed, wherein the epoxidation zone of (b) may comprise further epoxidation subzones which are arranged downstream of the first epoxidation subzone. If the first epoxidation subzone consisting of two or more epoxidation reactors A, it is preferred that the two or more epoxidation reactors A are arranged in parallel. In this case, it is preferred that in (b), the liquid feed stream provided in (a) is passed into at least one of the epoxidation reactors A. It is possible, for example, that, while the liquid feed stream provided in (a) is passed into at least one of the epoxidation reactors A, at least one of the reactors A is taken out of operation, for example for maintenance purposes and/or for regenerating the catalyst comprised in the at least one of the reactors A. If the first epoxidation subzone comprises two or more epoxidation reactors A, the reactors in operation are operated essentially identically so that in every epoxidation reactor A in operation, a given epoxidation condition is in the same range in every reactor.

The epoxidation conditions according to (b) comprise an epoxidation temperature TN, wherein TN is the temperature of a heat transfer medium used for adjusting the temperature of the reaction mixture in the first epoxidation reaction subzone according to (b) wherein it is preferred that said temperature is adjusted by passing the heat transfer medium through a jacket of the one or more epoxidation reactors A, wherein TN is preferably the temperature of the heat transfer medium prior to adjusting the temperature of the reaction mixture, preferably the temperature of the heat transfer medium at the entrance of the jacket of the one or more epoxidation reactors A. If the first epoxidation subzone comprises two or more epoxidation reactors A, the epoxidation temperature TN relates to the epoxidation temperature TN of a given reactor A in operation of first epoxidation subzone.

Preferably, the epoxidation conditions according to (b) comprise a first epoxidation reaction pressure in the range of from 14 to 100 bar, more preferably in the range of from 15 to 32 bar, more preferably in the range of from 15 to 25 bar. The first epoxidation reaction pressure is defined as the absolute pressure at the exit of the first epoxidation subzone. If the first epoxidation subzone comprises two or more epoxidation reactors A, the first epoxidation reaction pressure relates to the absolute pressures at the exit of a given reactor A in operation of first epoxidation subzone.

According to a first preferred embodiment of the present invention, the epoxidation zone according to (b) consists the first epoxidation subzone.

According to a second preferred embodiment of the present invention, the epoxidation zone according to (b) additionally comprises a second epoxidation subzone consisting of one or more epoxidation reactors B wherein, if the second epoxidation subzone comprises two or more epoxidation reactors B, the two or more epoxidation reactors B are arranged in parallel, wherein the second epoxidation subzone is arranged downstream of the first epoxidation subzone. In this case, it is preferred that in (b), the effluent stream obtained from the first epoxidation subzone, optionally after a suitable intermediate treatment, is passed into at least one of the epoxidation reactors B. It is possible, for example, that, while the effluent stream obtained from the first epoxidation subzone, optionally after a suitable intermediate treatment, is passed into at least one of the epoxidation reactors B, at least one of the reactors B is taken out of operation, for example for maintenance purposes and/or for regenerating the catalyst comprised in the at least one of the reactors B. If the second epoxidation subzone comprises two or more epoxidation reactors B, the reactors in operation are operated essentially identically so that in every epoxidation reactor B in operation, a given epoxidation condition is in the same range in every reactor. Generally, it is conceivable that in addition to the first epoxidation subzone and the second epoxidation subzone, the epoxidation zone according to (b) comprises at least one further epoxidation subzone arranged downstream of the second epoxidation subzone. Preferably, according to the second preferred embodiment of the present invention, the epoxidation zone according to (b) consists of the first epoxidation subzone and the second epoxidation subzone.

Preferably, the epoxidation conditions according to (b) comprise a second epoxidation reaction pressure in the range of from 14 to 100 bar, preferably in the range of from 14.5 to 32 bar, more preferably in the range of from 15 to 25 bar. The second epoxidation reaction pressure is defined as the absolute pressure at the exit of the second epoxidation subzone. If the second epoxidation subzone comprises two or more epoxidation reactors B, the second epoxidation reaction pressure relates to the absolute pressures at the exit of a given reactor B in operation of second epoxidation subzone.

Preferably, the epoxidation conditions according to (b) comprise an epoxidation catalyst loading in the second epoxidation subzone in the range of from 0.001 to 0.5 $h^{-1}$, more preferably in the range of from 0.005 to 0.3 $h^{-1}$, more preferably in the range of from 0.01 to 0.2 $h^{-1}$, wherein the epoxidation catalyst loading is defined as the ratio of the mass flow rate in kg/h of hydrogen peroxide contained in the feed stream passed into the second epoxidation subzone relative to the amount in kg of epoxidation catalyst comprising a titanium zeolite comprised in the second epoxidation subzone according to (b).

Preferably, the temperature of the reaction mixture in the second epoxidation reaction subzone is not adjusted by passing a heat transfer medium through a jacket of the one or more epoxidation reactors B. More preferably, the second epoxidation subzone is an essentially adiabatic epoxidation subzone. More preferably, the second epoxidation subzone is an adiabatic epoxidation subzone.

According to (b), the liquid feed stream provided in (a) is passed into an epoxidation zone comprising an epoxidation catalyst comprising a titanium zeolite. Preferably, the titanium zeolite comprised in the epoxidation catalyst is a titanium zeolite having ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EPI, ERI, ESV, ETR, EUO, FAU, FER, FRA, GIS, GIU, GME, GON, GOO, HEU, IFR, ISV, ITE, ITH, ITW, IWR, IWW, JBW, KFI, LAU, LEV, LIO, LOS, LOV, LTA, LTL, LTN, MAR, MAZ, MEI, MEL, MEP, MER, MMFI, MFS, MON, MOR, MSO, MTF, MTN, MTT, MTW, MWW, NAB, NAT, NEES, NON, NPO, OBW, OFF, OSI, OSO, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN SFO, SGT, SOD, SSY, STF, STI, STT, TER, THO, TON, TSC, UEI, UFI, UOZ, USI, UTL, VET, VFI, VNI, VSV, WEI, WEN, YUG, ZON framework structure or a mixed structure of two or more of these framework structures, preferably a titanium zeolite having an MFI framework structure, an MEL framework structure, an MWW framework structure, an ITQ framework structure, a BEA framework structure, a MOR framework structure, or a mixed structure of two or more of these framework structures, preferably an MWW framework structure.

More preferably, the titanium zeolite, preferably the titanium zeolite having an MWW framework structure, comprises at least one of Al, B, Zr, V, Nb, Ta, Cr, Mo, W, Mn, Fe, Co, Ni, Zn, Ga, Ge, In, Sn, Pb, Pd, Pt, Au, preferably at least one of B, Zr, V, Nb, Ta, Cr, Mo, W, Mn, Fe, Co, Ni, Zn, Ga, Ge, In, Sn, Pb, Pd, Pt, Au, more preferably Zn.

In one preferred embodiment, the titanium zeolite is an aluminum-free zeolitic material of MWW framework structure, containing titanium, preferably in an amount of from 0.5 to 5 weight-%, more preferably from 1 to 2 weight-%, calculated as elemental titanium and based on the total weight of the titanium containing zeolite, and containing zinc, preferably in an amount of from 0.5 to 5 weight-%, preferably from 1 to 2 weight-%, calculated as elemental zinc and based on the total weight of the titanium containing zeolite. The term "aluminum-free" in the context of the present invention refers to an embodiment according to which the aluminum content of the zeolitic material is 0.05 weight-ppm at most, preferably 0.03 weight-ppm at most, more preferably 0.02 weight-ppm at most, based on the total weight of zeolitic material. The weight-%-values refer to an embodiment according to which the zeolitic material is in dry state, preferably after drying for at least ten hours at 80° C. at a pressure of less than 1013.25 hPa.

The epoxidation catalyst comprising a titanium zeolite can be employed in every conceivable form, including a powder, a micropowder, preferably a spray-powder, as a molding comprising a powder, or as a molding comprising a micropowder, preferably a spray-powder. Preferably, the catalyst comprising the titanium zeolite is employed as a molding comprising a powder or a micropowder, preferably a spray-powder, more preferably as a molding comprising a micropowder, preferably a spray-powder. More preferably, the catalyst comprising the titanium zeolite is present in the epoxidation zone as a molding, preferably as fluidized-bed catalyst or a fixed-bed catalyst, more preferably as a fixed-bed catalyst.

The process is preferably a continuous process.

The present invention is further illustrated by the following set of embodiments and combinations of embodiments resulting from the given dependencies and back-references.

1. A process for purifying propylene oxide, comprising
   (i) providing a stream S0 comprising propylene oxide, acetonitrile, water, and an organic compound comprising a carbonyl group —C(=O)—, wherein said organic compound comprising a carbonyl group —C(=O)— comprises one or more of acetone and propionaldehyde;
   (ii) separating propylene oxide from the stream S0 by distillation, comprising subjecting the stream S0 to distillation conditions in a distillation column, obtaining a gaseous top stream S1c which is enriched in propylene oxide compared to the stream S0, a liquid bottoms stream S1a which is enriched in acetonitrile and water compared to the stream S0, and a side stream S1b comprising propylene oxide which is enriched in the carbonyl compound compared to the stream S0;

wherein the distillation column is operated at an absolute pressure at the top of the distillation column in the range of from 0.1 to 2.0 bar and an internal reflux ratio in the range of from 2.0 to 6.0;

wherein the distillation column exhibits at least 100 theoretical trays, the rectifying section of the distillation column consists of from 30 to 70%, preferably of from 40 to 60%, of the theoretical trays and the stripping section of the distillation column consists of from 70 to 30%, preferably of from 60 to 40%, of the theoretical trays.

2. The process of embodiment 1, wherein the distillation column is operated at an absolute pressure at the top of the distillation column in the range of from 0.2 to 1.5 bar, preferably in the range of from 0.3 to 1.0 bar, more preferably in the range of from 0.45 to 0.55 bar.

3. The process of embodiment 1 or 2, wherein the distillation column is operated at a reflux ratio in the range of from 2.0 to 5.5, preferably in the range of from 3.0 to 5.0, more preferably in the range of from 3.5 to 4.5.

4. The process of any one of embodiments 1 to 3, wherein the distillation column exhibits from 100 to 150, preferably from 105 to 145, more preferably from 110 to 140, more preferably from 115 to 135, more preferably from 120 to 130 theoretical trays.

5. The process of any one of embodiments 1 to 4, wherein the distillation column is operated at an absolute pressure at the top of the column in the range of from 0.45 to 0.55 bar and a reflux ratio in the range of from 3.5 to 4.5, and wherein the distillation column exhibits from 120 to 130 theoretical trays.

6. The process of any one of embodiments 1 to 5, wherein the side stream S1b is removed from the rectifying section of the distillation column.

7. The process of any one of embodiments 1 to 6, wherein the side stream S1b is removed from the rectifying section of the distillation column at a position which is at least 1 theoretical tray above the stripping section of the distillation column.

8. The process of any one of embodiments 1 to 7, wherein the side stream S1b is removed from the rectifying section of the distillation column at a position which is from 1 to 20, preferably from 2 to 19, more preferably from 3 to 18, more preferably from 4 to 17, more preferably from 5 to 16, more preferably from 5 to 15 theoretical tray above the stripping section of the distillation column.

9. The process of any one of embodiments 1 to 8, wherein the organic compound comprising a carbonyl group comprised in the stream S0 further comprises one or more further aldehydes, one or more further ketones, or a mixture of one or more further aldehydes and one or more further ketones.

10. The process of any one of embodiments 1 to 9, wherein the organic compound comprising a carbonyl group comprised in the stream S0 further comprises one or more of acetaldehyde, formaldehyde, butyraldehyde, isobutyraldehyde, 2-butanon, 1-pentanal, 2-pentanon, 3-pentanon, 2-methylpentanone, preferably one ore more of acetaldehyde, formaldehyde, butyraldehyde, isobutyraldehyde, more preferably at least acetaldehyde.

11. The process any one of embodiments 1 to 10, wherein at least 95 weight-%, preferably at least 98 weight-%, more preferably at least 99 weight-% of the stream S0 consist of propylene oxide, acetonitrile, water, and the organic compound comprising a carbonyl group.

12. The process of any one of embodiments 1 to 11, wherein the stream S0 comprises the propylene oxide in amount of from 5 to 15 weight-%, preferably from 8 to 12 weight-%, based on the total weight of the stream S0; the acetonitrile in an amount of from 60 to 80 weight-%, preferably from 65 to 75 weight-%, based on the total weight of the stream S0; the water in amount of from 10 to 25 weight-%, preferably from 17 to 21 weight-%, based on the total weight of the stream S0; propionaldehyde in an amount of from 100 to 300 weight-ppm, preferably from 150 to 250 weight-ppm, based on the total weight of the stream S0; acetone in an amount of from 60 to 200 weight-ppm, preferably from 80 to 120 weight-ppm, based on the total weight of the stream S0; and acetaldehyde in an amount of from 80 to 300 weight-ppm, preferably from 100 to 200 weight-ppm, based on the total weight of the stream S0.

13. The process of any one of embodiments 1 to 12, wherein the stream S0 is obtainable or obtained by a process comprising
(a) providing a stream comprising propene and preferably propane, hydrogen peroxide or a source of hydrogen peroxide, water, and acetonitrile;
(b) passing the liquid feed stream provided in (a) into an epoxidation zone comprising an epoxidation catalyst comprising a titanium zeolite, and subjecting the liquid feed stream to epoxidation reaction conditions in the epoxidation zone, obtaining a reaction mixture comprising propene and preferably propane, propylene oxide, water, acetonitrile, and the organic compound comprising a carbonyl group;
(c) removing an effluent stream from the epoxidation zone, the effluent stream comprising propylene oxide, water, acetonitrile, propene and preferably propane, and the organic compound comprising a carbonyl group;
(d) separating propene and preferably propane from the effluent stream by distillation, comprising subjecting the effluent stream to distillation conditions in a distillation unit, obtaining a gaseous stream which is enriched in propene and preferably propane compared to the effluent stream subjected to distillation conditions, and a liquid bottoms stream which is enriched in propylene oxide, water, acetonitrile and the organic compound comprising a carbonyl group compared to the effluent stream subjected to distillation conditions;
wherein said liquid bottoms stream obtained according to (d) is the stream S0.

14. The process of any one of embodiments 1 to 12, wherein providing the stream S0 according to (i) comprises
(a) providing a stream comprising propene and preferably propane, hydrogen peroxide or a source of hydrogen peroxide, water, and acetonitrile;
(b) passing the liquid feed stream provided in (a) into an epoxidation zone comprising an epoxidation catalyst comprising a titanium zeolite, and subjecting the liquid feed stream to epoxidation reaction conditions in the epoxidation zone, obtaining a reaction mixture comprising propene and preferably propane, propylene oxide, water, acetonitrile, and the organic compound comprising a carbonyl group;
(c) removing an effluent stream from the epoxidation zone, the effluent stream comprising propylene oxide, water, acetonitrile, propene and preferably propane, and the organic compound comprising a carbonyl group;

(d) separating propene and preferably propane from the effluent stream by distillation, comprising subjecting the effluent stream to distillation conditions in a distillation unit, obtaining a gaseous stream which is enriched in propene and preferably propane compared to the effluent stream subjected to distillation conditions, and a liquid bottoms stream which is enriched in propylene oxide, water, acetonitrile and the organic compound comprising a carbonyl group compared to the effluent stream subjected to distillation conditions; wherein said liquid bottoms stream obtained according to (d) is the stream S0.

15. The process of embodiment 13 or 14, wherein the effluent stream removed according to (c) further comprises oxygen, wherein (d) comprises separating oxygen, propene and preferably propane from the effluent stream by distillation, comprising subjecting the effluent stream to distillation conditions in a distillation unit, obtaining a gaseous stream which is enriched in oxygen, propene and preferably propane compared to the effluent stream subjected to distillation conditions, and a liquid bottoms stream which is enriched in propylene oxide, water and acetonitrile compared to the effluent stream subjected to distillation conditions.

16. The process of any one of embodiments 13 to 15, wherein prior to (d), the effluent stream removed according to (c) is depressurized.

17. The process of embodiment 16, wherein from depressurizing the effluent stream, a gaseous stream and a liquid stream are obtained and wherein preferably the gaseous and liquid streams are passed separately to the distillation unit, preferably the distillation tower, employed according to (d), more preferably to different theoretical trays of the distillation tower employed according to (d).

18. The process of any one of embodiments 1 to 17, wherein the top stream S1c obtained in (ii) contains at least 99.00 weight-%, more preferably at least 99.50 weight-%, more preferably at least 99.80 weight-%, propylene oxide based on the total weight of the stream S1c.

19. The process of any one of embodiments 1 to 18, wherein the top stream S1c obtained in (ii) contains at the outmost 50 weight-ppm, preferably at the outmost 25 weight-ppm, more preferably at the outmost 20 weight-ppm of the organic compound comprising a carbonyl group based on the total weight of the stream S1c.

20. The process of any one of embodiments 1 to 19, wherein the top stream S1c obtained in (ii) contains less than 20 weight-ppm, preferably less than 15 weight-ppm, propionaldehyde based on the total weight of the stream S1c.

21. The process of any one of embodiments 1 to 20, wherein the top stream S1c obtained in (ii) contains less than 10 weight-ppm, preferably less than 5 weight-ppm acetone based on the total weight of the stream S1c.

22. The process of any one of embodiments 1 to 21, wherein the top stream S1c obtained in (ii) contains at the outmost 100 weight-ppm, preferably at the outmost 75 weight-ppm, more preferably at the outmost 50 weight-ppm water based on the total weight of the stream S1c.

23. The process of any one of embodiments 1 to 22, wherein the top stream S1c obtained in (ii) comprises the propylene oxide in an amount of at least 99.00 weight-%, more preferably at least 99.50 weight-%, more preferably at least 99.80 weight-%, propylene oxide, based on the total weight of the stream S1c; the organic compound comprising a carbonyl group in an amount of at the outmost 50 weight-ppm, preferably at the outmost 25 weight-ppm, more preferably at the outmost 20 weight-ppm, based on the total weight of the stream S1c; and water in an amount of at the outmost 100 weight-ppm, preferably at the outmost 75 weight-ppm, more preferably at the outmost 50 weight-ppm, based on the total weight of the stream S1c.

24. The process of any one of embodiments 1 to 23, wherein the top stream S1c obtained in (ii) comprises the propylene oxide in an amount of at least 99.00 weight-%, more preferably at least 99.50 weight-%, more preferably at least 99.80 weight-%, propylene oxide, based on the total weight of the stream S1c; propionaldehyde in an amount of less than 20 weight-ppm, preferably less than 15 weight-ppm, based on the total weight of the stream S1c; acetone in an amount of less than 10 weight-ppm, preferably less than 5 weight-ppm, based on the total weight of the stream S1c; and water in an amount of at the outmost 100 weight-ppm, preferably at the outmost 75 weight-ppm, more preferably at the outmost 50 weight-ppm, based on the total weight of the stream S1c.

25. The process of any one of embodiments 1 to 24, wherein bottoms stream S1a contains the organic compound comprising a carbonyl group in an amount of at most 20 weight-ppm, preferably at most 10 weight-ppm, more preferably at most 2 weight-ppm, based on the weight of S1a.

26. The process of any one of embodiments 1 to 25, wherein bottoms stream S1a contains propionaldehyde in an amount of at most 10 weight-ppm, preferably at most 5 weight-ppm, more preferably at most 1 weight-ppm, based on the weight of S1a.

27. The process of any one of embodiments 1 to 26, wherein bottoms stream S1a contains acetone in an amount of at most 10 weight-ppm, preferably at most 5 weight-ppm, more preferably at most 1 weight-ppm, based on the weight of S1a.

28. The process of any one of embodiments 1 to 27, wherein at least 95 weight-% of bottoms stream S1a consist of acetonitrile and water, wherein preferably, the weight ratio of acetonitrile relative to water in the stream S1a is greater than 1:1.

29. The process of any one of embodiments 1 to 28, wherein bottoms stream S1a contains at most 10 weight-ppm, preferably at most 5 weight-ppm, more preferably at most 1 weight-ppm, of the propylene oxide, based on the weight of S1a.

30. The process of any one of embodiments 1 to 29, wherein bottoms stream S1a comprises the acetonitrile in an amount of from 70 to 80 weight-%, based on the weight of S1a; water in an amount of from 10 to 30 weight-% based on the weight of stream S1a; at most 10 weight-ppm, preferably at most 5 weight-ppm, more preferably at most 1 weight-ppm, of the propylene oxide, based on the weight of stream S1a; and each of propionaldehyde and acetone in an amount of at most 10 weight-ppm, preferably at most 5 weight-ppm, more preferably at most 1 weight-ppm, based on the weight of stream S1a.

31. The process of any one of embodiments 1 to 30, wherein a part of bottoms stream S1a is introduced to the distillation unit employed for the separation in (d) according to any one of embodiments 13 to 15 as extracting agent, preferably in the upper part of the distillation unit.

32. The process of any one of embodiments 1 to 31, wherein the side stream S1b comprises the organic compound comprising a carbonyl group in an amount of 10 weight- %, preferably 15 weight-%; based on the total weight of the side stream S1 b; wherein the organic compound comprising a carbonyl group preferably comprises propionaldehyde in an amount of 10 weight-% based on the total weight of the side stream S1b and acetone in an amount of weight-% based on the total weight of the side stream S1b.
33. The process of any one of embodiments 1 to 32, wherein at least 95 weight-%, preferably at least 98 weight-%, more preferably at least 99 weight-% of the side stream S1b consist of propylene oxide, acetonitrile, water, and the organic compound comprising a carbonyl group.
34. The process of any one of embodiments 1 to 33, wherein the side stream S1b comprises the propylene oxide in an amount of from 60 to 80 weight-%, preferably from 65 to 75 weight-%, based on the total weight of the side stream S1 b; the acetonitrile in an amount of from 2 to 6 weight-%, preferably from 3.5 to 5.5 weight-%, based on the total weight of the side stream S1 b; the organic compound comprising a carbonyl group in an amount of from 10 to 30 weight-%, preferably from 15 to 25 weight-%; based on the total weight of the side stream S1b; wherein the organic compound comprising a carbonyl group preferably comprises propionaldehyde in an amount of from 10 to 20 weight-%, preferably from 12 to 16 weight-%, based on the total weight of the side stream S1 b, and acetone in an amount of from 5 to 10 weight-%, preferably from 5 to 9 weight-%, based on the total weight of the side stream S1 b.
35. The process of any one of embodiments 1 to 34, which is a continuous process.

The present invention is further illustrated by the following reference examples, comparative examples, and examples.

EXAMPLES

Reference Example 1: Preparation of a Catalyst Comprising a Titanium Zeolite Having Framework Type MWW 1.1 Preparation of Boron Containing Zeolite of Structure MWW (BMWW)

A 2 m³ stirred tank reactor was first loaded with 470.4 kg of deionized water. After starting the stirrer at 70 rpm, boric acid (162.5 kg) was added and the suspension was stirred for 3 h. Subsequently, piperidine (272.5 kg) was added at once causing the temperature to rise from 28° C. to 46° C. To this solution colloidal silica (Ludox® AS040, 392.0 kg) was added. The reactor was then slowly heated to 170° C. within 5 hours and then kept at this temperature under stirring for 120 hours. The maximum pressure during the reaction was 9.3 bar. Afterwards the reactor was cooled down to 50° C. The gel obtained had a pH of 11.3 and a viscosity of 15 mPa·s at 20° C. The gel was then filtered and the filter cake washed with deionized water until the conductivity of the washings was below 500 microSiemens/cm. The filter cake was then suspended in deionized water and the suspension was spray-dried at 235° C. using nitrogen as the carrier gas. The white powder obtained (174.3 kg) contained 3.5 weight-% water. This white powder was then calcined at 650° C. in a rotary kiln to give 138.2 kg of boron containing zeolite of structure type MWW (BMWW) as a white powder.

1.2 Deboronation of BMWW with Water

A 5 m³ stirred tank reactor was loaded with 125 kg of the BMWW obtained according to the previous step 1.1 and 3750 kg of deionized water. The reactor was then slowly heated to 100° C. within 1 hour under stirring at 70 rpm, and then kept at this temperature for 20 hours and finally cooled to a temperature below 50° C. before it was filtered. The filter cake was then washed with deionized water until the washings had conductivity below 15 microSiemens/cm. The filter cake was then dried for 6 hours under a nitrogen stream. The filter cake was then removed and suspended in 850 kg of deionized water. This suspension was then spray-dried at 235° C. using nitrogen as the carrier gas. The spray dried material weighed 118.5 kg and contained 42.5 weight-% Si, 0.06 weight-% B and 0.23 weight-% C (total organic carbon, TOC).

1.3 Preparation of Titanium Containing Zeolite of Structure Type MWW (TiMWW)

A 2 m³ stirred tank reactor was first loaded with 111.2 kg of the spray-dried material from the previous step 1.2. In a separate 2 m³ stirred tank reactor were placed 400 kg of deionized water. After starting the stirrer at 80 rpm, piperidine (244.0 kg) was added. After the addition of piperidine was finished the mixture was stirred for 5 minutes before tetrabutyl orthotitanate (22.4 kg) was added. The pipe through which the titanate was added was then flushed with 40 kg of deionized water. The mixture was then stirred for 1 hour before being added to the first stirred tank reactor containing the spray-dried powder under stirring (50 rpm). The reactor was then heated to 170° C. and kept at this temperature for 120 h before being cooled to 50° C. The maximum pressure during the reaction was 10.6 bar. The cooled suspension was then filtered and the filter cake was washed with deionized water until the washings had conductivity below 1300 microSiemens/cm and an approximately neutral pH value. The filter cake was then dried under a nitrogen stream for 6 hours. The filter cake containing about 80 weight-% of water was used directly for the next step. The filter cake from the previous step and 1000 kg of deionized water were filled in a 2 m³ stirred tank reactor. Then 1900 kg of nitric acid (53 weight-% in water) were added under stirring at 70 rpm. The reactor was then heated to 100° C. and kept at this temperature for 20 hours before being cooled to 50° C. The suspension obtained was then filtered and the filter cake was washed with deionized water until the conductivity was below 10 microSiemens/cm and the washings were approximately neutral. Subsequently the filter cake was dried under a stream of nitrogen for 6 hours. This filter cake was then suspended in water and spray-dried at 235° C. using nitrogen as the carrier gas. 96 kg of a spray-dried powder were obtained. This material was then calcined in a rotary kiln at 650° C. 84 kg of titanium zeolite of structure type MWW (TiMWW) were obtained as a powder containing 43 weight-% Si, 2.0 weight-% Ti and 0.2 weight-% C (TOC). The pore volume determined by Hg-porosimetry according to DIN 66133 was 7.3 ml/g and the BET surface area determined according to DIN 66131 was 467 m²/g.

1.4 Preparation of a Zinc Containing TiMWW (Zn-TiMWW) by Impregnation
a) In a vessel equipped with a reflux condenser, a solution of 981 kg deionized water and 6.0 kg zinc acetate dihydrate was prepared within 30 min. Under stirring (40 r.p.m.), 32.7 kg of the calcined Ti-MWW material obtained according to 1.3 above were suspended. Subsequently, the vessel was closed and the reflux condenser put into operation. The stirring rate was increased to 70 r.p.m.
b) In a vessel equipped with a reflux condenser, a solution of 585 kg deionized water and 3.58 kg zinc acetate dihydrate was prepared within 30 min. Under stirring (40 r.p.m.), 19.5 kg of the calcined Ti-MWW material obtained according to 1.3 above were suspended. Subsequently, the vessel was closed and the reflux condenser put into operation. The stirring rate was increased to 70 r.p.m.

In all batches a) and b), the mixture in the vessel was heated to 100° C. within 1 h and kept under reflux for 2 h at a stirring rate of 70 r.p.m. Then, the mixture was cooled within 2 h to a temperature of less than 50° C. For each batch a) and b), the cooled suspension was subjected to filtration, and the mother liquor was transferred to waste water discharge. The filter cake was washed five times with deionized water under a nitrogen pressure of 2.5 bar. After the last washing step, the filter cake was dried in a nitrogen stream for 10 h. In total 297 kg of nitrogen dried filter cake were obtained. The thus dried Zn-impregnated TiMWW material (ZnTiMWW), had a Si content of 42 weight-%, a Ti content of 1.8 weight-%, a Zn content of 1.3 weight-.%.

From 297 kg of the mixture of the filter cake obtained above, an aqueous suspension was prepared with deionized water, the suspension having a solid content of 15 weight-%. This suspension was subjected to spray-drying in a spray-tower with the following spray-drying conditions:
- apparatus used: spray tower with one nozzle
- operation mode: nitrogen straight
- configuration: dehumidifier—filter—scrubber
- dosage: flexible-tube pump VF 10 (supplier: Verder)
- nozzle with a diameter of 4 mm (supplier: Niro)
- filter material: Nomex® needle-felt 10 m²

|  |  | Runtime/h |  |  |  |  |
|---|---|---|---|---|---|---|
|  |  | 0.5 | 1.5 | 2.5 | 3.5 | 4.5 |
|  | Flow rate gas/(kg/h) | 550 | 550 | 550 | 550 | 550 |
| Temperature drying gas/° C. | spray tower (in) | 305 | 305 | 305 | 305 | 305 |
|  | spray tower (out) | 151 | 151 | 151 | 151 | 151 |
|  | Filter (in) | 140 | 137 | 130 | 127 | 126 |
|  | Scrubber (in) | 110 | 110 | 110 | 108 | 105 |
|  | Scrubber (out) | 14 | 14 | 15 | 15 | 15 |
| Differential pressure/ mbar | spray tower | 3.1 | 3 | 3 | 2.8 | 2.9 |
|  | Filter | 1.7 | 1.7 | 1.8 | 1.8 | 2.1 |
|  | Scrubber | 3.8 | 4.1 | 4.2 | 4.2 | 4.2 |
| Pressure/ mbar | spray tower | −103 | −1.2 | −0.9 | −0.9 | −1.1 |
| Nozzle gas | Flow rate kg/h | 23 | 23 | 23 | 23 | 23 |
|  | Temperature/° C. | r.t.*) | r.t.*) | r.t.*) | r.t.*) | r.t.*) |
|  | Pressure/bar | 2.5 | 2.5 | 2.5 | 2.5 | 2.5 |
| Spray-dried product | Temperature/° C. | r.t.*) | r.t.*) | r.t.*) | r.t.*) | r.t.*) |

*)room temperature

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening. The spray-dried material thus obtained had a Zn content of 1.4 weight-%, a Ti content of 1.7 weight-%, a Si content of 41 weight-%, and a TOC content of <0.5 weight-%. The spray-dried product was then subjected to calcination for 2 h at 650° C. under air in a rotary furnace, yielding 43.8 kg of calcined spray-dried ZnTiMWW. The calcined spray-dried material thus obtained had a Zn content of 1.3 weight-%, a Ti content of 1.8 weight-%, a Si content of 42.5 weight-%, and a C content of <0.1 weight-%. The bulk density of the calcined spray-dried ZnTiMWW was 90 g/l (gram/liter). The mesopores of the micropowder had an average pore diameter (4V/A) of 20.2 nm as determined by Hg porosimetry according to DIN 66133. The macropores of the micropowder had an average pore diameter (4V/A) of 67.6 nm as determined by Hg porosimetry according to DIN 66133. The micropores of the ZnTiMWW contained in the micropowder had an average pore diameter of 1.06 nm as determined by nitrogen adsorption according to DIN 66134 (Horward-Kawazoe method). The Dv10 value of the particles of the micropowder was 4.10 micrometers. The Dv50 value of the particles of the micropowder was 8.19 micrometers. The Dv90 value of the particles of the micropowder was 14.05 micrometers. The degree of crystallization determined via XRD was (77+/−10) %, the average crystallite size 35.0 nm+/−10%. It was found that the crystalline phase exhibits a pure MWW structure. No other crystalline titania phases such as anatase, rutile or brookite, or crystalline zinc silicate ($Zn_2SiO_4$) such as willemite could be detected.

1.5 Preparation of Moldings Containing ZnTiMWW and Silica Binder

Starting from the calcined spray-dried ZnTiMWW material obtained according to 1.4 above, a molding was prepared, dried, and calcined. Therefor, 12 batches were prepared, each starting from 3.5 kg of the calcined spray-dried ZnTiMWW material obtained above, 0.226 kg Walocel™ (Walocel MW 15000 GB, Wolff Cellulosics GmbH & Co. KG, Germany), 2.188 kg Ludox® AS-40 and 6.6 l deionized water, as follows:

3.5 kg ZnTiMWW and 0.226 kg Walocel were subjected to kneading in an edge mill for 5 min. Then, during further kneading, 2.188 kg Ludox were added continuously. After another 10 min, addition of 6 l of deionized water was started. After another 30 min, further 0.6 l of deionized water were added. After a total time of 50 min, the kneaded mass had become extrudable. Thereafter, the kneaded mass was subjected to extrusion under 65-80 bar wherein the extruder was cooled with water during the extrusion process. Per batch, the extrusion time was in the range of from 15 to 20 min. The power consumption per batch during extrusion was 2.4 A. A die head was employed allowing for producing cylindrical strands having a diameter of 1.7 mm. At the die head out outlet, the strands were not subjected to a cutting to length. The strands thus obtained were dried for 16 h at 120° C. in a drying chamber under air. In total (sum of the 12 batches), 56 kg white strands with a diameter of 1.7 mm were obtained. 56 kg of the dried strands were subjected to calcination in a rotary furnace at 550° C. for 1 h under air, yielding 52 kg calcined strands. Thereafter, the strands were sieved (mesh size 1.5 mm), and the yield, after sieving, was 50.0 kg. The thus obtained moldings exhibited a bulk density of 322 g/l (gram per liter) and had a Zn content of 1.1 weight-%, a Ti content of 1.4 weight-%, a Si content of 43 weight-%, and a C content of <0.1 weight-%. The mesopores of the micropowder had an average pore diameter (4V/A) of 20.9 nm as determined by Hg porosimetry according to DIN 66133. The macropores of the micropowder had an average pore diameter (4V/A) of 50.0 nm as determined by Hg porosimetry according to DIN 66133. The degree of crystallization determined via XRD was (70+/−10) %, the average crystallite size 32.5 nm+/−10%. The crush strength of the moldings as determined according to the method using a crush strength test machine Z2.5/TS01S was 4.4 N (standard deviation: 0.5 N). The minimum value found when testing the 10 samples was 3.5 N, the maximum value 5.1 N. In the $^{29}$Si MAS NMR, after the curve had been deconvolved by the proper Gaussian-Lorentzian line shapes, six peaks were clearly observed. The $Q^3/Q^4$ ratio was found to be 2.2. The total amount of adsorbed water as determined according to Reference Example 6 of the molding was 6.9 weight-%. The Langmuir surface are determined via nitrogen adsorption at 77 K according to DIN 66133 was 518 m$^2$/g, the mulitpoint BET specific surface area determined via nitrogen adsorption at 77 K according to DIN 66133 was 373 m$^2$/g. The total intrusion volume determined according to Hg porosimetry according to DIN 66133 was 1.3 ml/g (milliliter/gram), the respective total pore area 100.2 m$^2$/g. It was found that the crystalline phase of the moldings exhibits a pure MWW structure. No other crystalline titania phases such as anatase, rutile or brookite, or crystalline zinc silicate ($Zn_2SiO_4$) such as willemite could be detected via XRD.

Starting from the calcined strands, a post-treatment stage was performed as follows: 1,000 kg deioinized water were filled in a vessel. Then, 50 kg of the calcined moldings were added. The vessel was closed (pressure-tight), and the obtained mixture was heated to a temperature of 145° C. within 1.5 h and kept at this temperature under autogenous pressure (about 3 bar) for 8 h. Then, the mixture was cooled for 2 h. The water-treated strands were subjected to filtration and washed with deionized water. The obtained strands were heated in a drying chamber under air within 1 h to a temperature of 120° C. and kept at this temperature for 16 h. Subsequently, the dried material was heated under air to a temperature of 450° C. within 5.5 h and kept at this temperature for 2 h. Thereafter, the strands were sieved (mesh size 1.5 mm), and the yield, after sieving, was 49.1 kg. The thus obtained water-treated moldings exhibited a bulk density of 332 g/l (gram per liter) and had a Zn content of 1.1 weight-%, a Ti content of 1.4 weight-%, a Si content of 42 weight-%, and a C content of <0.10 weight-%. The mesopores of the micropowder had an average pore diameter (4V/A) of 22.1 nm as determined by Hg porosimetry according to DIN 66133. The macropores of the micropowder had an average pore diameter (4V/A) of 52.0 nm as determined by Hg porosimetry according to DIN 66133. The degree of crystallization determined via XRD was (69+/−10) %, the average crystallite size 30.5 nm+/−10%. The crush strength of the moldings as determined according to the method using a crush strength test machine Z2.5/TS01S was 13.7 N (standard deviation: 2.5 N). The minimum value found when testing the 10 samples was 10.2 N, the maximum value 17.6 N. In the $^{29}$Si MAS NMR, after the curve had been deconvolved by the proper Gaussian-Lorentzian line shapes, six peaks were clearly observed. The $Q^3/Q^4$ ratio was found to be 1.39. The total amount of adsorbed water of the molding was 6.9 weight-%. The intensity ratio of the infrared band in the region of (3746+/−20) cm$^{-1}$ attributed to the free silanol groups, relative to the infrared band in the region of 3688+/−20 cm$^{-1}$ attributed to vicinal silanol groups was smaller than 1.4. The Langmuir surface are determined via nitrogen adsorption at 77 K according to DIN 66133 was 421 m$^2$/g, the multipoint BET specific surface area determined via nitrogen adsorption at 77 K according t DIN 66133 was 303 m$^2$/g. The total intrusion volume determined according to Hg porosimetry according to DIN 66133 was 1.3 ml/g (milliliter/gram), the respective total pore area 98.7 m$^2$/g. It was found that the crystalline phase of the moldings exhibits a pure MWW structure. No other crystalline titania phases such as anatase, rutile or brookite, or crystalline zinc silicate ($Zn_2SiO_4$) such as willemite could be detected via XRD.

Reference Example 2: Characterization of the Catalyst

Reference Example 2.1: Determination of Dv10, Dv50, and Dv90 Values 1.0 g of the micropowder is suspended in 100 g deionized water and stirred for 1 min. The sample was subjected to the measurement in an apparatus using the following parameters: Mastersizer S long bed version 2.15, ser. No. 33544-325; supplier: Malvern Instruments GmbH, Herrenberg, Germany: focal width 300RF mm; beam length 10.00 mm; module MS017; shadowing 16.9%; dispersion model 3$$D; analysis model polydisperse correction none.

Reference Example 2.2: Determination of the Silanol Concentration of the Moldings of the Present Invention For the determination of the silanol concentration, the $^{29}$Si MAS NMR experiments were carried out at room temperature on a VARIAN Infinityplus-400 spectrometer using 5.0 mm $ZrO_2$ rotors. The $^{29}$Si MAS NMR spectra were collected at 79.5 MHz using a 1.9 µs π/4 (microsecond pi/4) pulse with 10 s recycle delay and 4000 scans. All $^{29}$Si spectra were recorded on samples spun at 6 kHz, and chemical shifts were referenced to 4,4-dimethyl-4-silapentane sulfonate sodium (DSS). For the determination of the silanol group concentration, a given $^{29}$Si MAS NMR spectrum is deconvolved by the proper Gaussian-Lorentzian line shapes. The concentration of the silanol groups with respect to the total number of Si atoms is obtained by integrating the deconvolved $^{29}$Si MAS NMR spectra.

Reference Example 2.3: Determination of the Crush Strength of the Moldings

The crush strength as referred to in the context of the present invention is to be understood as determined via a crush strength test machine Z2.5/TS01S, supplier Zwick GmbH & Co., D-89079 Ulm, Germany. As to fundamentals of this machine and its operation, reference is made to the respective instructions handbook "Register 1: Betriebsanleitung/Sicherheitshandbuch für die Material-Prüfmaschine Z2.5/TS01S", version 1.5, December 2001 by Zwick GmbH & Co. Technische Dokumentation, August-Nagel-Strasse 11, D-89079 Ulm, Germany. With said machine, a given strand is subjected to an increasing force via a plunger having a diameter of 3 mm until the strand is crushed. The force at which the strand crushes is referred to as the crushing strength of the strand. The machine is equipped with a fixed horizontal table on which the strand is positioned. A plunger which is freely movable in vertical direction actuates the strand against the fixed table. The apparatus was operated with a preliminary force of 0.5 N, a shear rate under preliminary force of 10 mm/min and a subsequent testing rate of 1.6 mm/min. The vertically movable plunger was connected to a load cell for force pick-up and, during the measurement, moved toward the fixed turntable on which the molding (strand) to be investigated is positioned, thus actuating the strand against the table. The plunger was applied to the stands perpendicularly to their longitudinal axis. Controlling the experiment was carried out by means of a computer which registered and evaluated the results of the measurements. The values obtained are the mean value of the measurements for 10 strands in each case.

Reference Example 2.4: $^{29}$Si Solid-State NMR Spectra Regarding $Q^3$ and $Q^4$ Structures The effect of the inventive water treatment on the molding related to $Q^3$ and $Q^4$ structures in the material was characterized by comparing the changes in $^{29}$Si solid-state NMR spectra under comparable conditions. All $^{29}$Si solid-state NMR experiments were performed using a Bruker Advance spectrometer with 300 MHz $^1$H Larmor frequency (Bruker Biospin, Germany). Samples were packed in 7 mm $ZrO_2$ rotors, and measured under 5 kHz Magic Angle Spinning at room temperature. $^{29}$Si direct polarization spectra were obtained using (pi/2)-pulse excitation with 5 microsecond pulse width, a $^{29}$Si carrier frequency corresponding to −65 ppm in the spectrum, and a scan recycle delay of 120 s. Signal was acquired for 25 ms under 45 kHz high-power proton decoupling, and accumulated over 10 to 17 hours. Spectra were processed using Bruker Topspin with 30 Hz exponential line broadening, manual phasing, and manual baseline correction over the full spectrum width. Spectra were referenced with the polymer Q8M8 as an external secondary standard, setting the resonance of the trimethyl-silyl M group to 12.5 ppm. The spectra were then fitted with a set of Gaussian line shapes, according to the number of discernable resonances. Relating to the presently assessed spectra, 6 lines in total were used, accounting for the five distinct peak maxima (at approximately −118, −115, −113, −110 and −104 ppm) plus the clearly visible shoulder at −98 ppm. Fitting was performed using DMFit (Massiot et al., Magnetic Resonance in Chemistry, 40 (2002) pp 70-76). Peaks were manually set at the visible peak maxima or shoulder. Both peak position and line width were then left unrestrained, i.e., fit peaks were not fixed at a certain position. The fitting outcome was numerically stable, i.e., distortions in the initial fit setup as described above did lead to similar results. The fitted peak areas were further used normalized as done by DMFit. After the water treatment of the invention, a decrease of signal intensity at the left hand side of the spectrum was observed, a region that includes $Q^3$ silanol structures (here especially: around and above −104 ppm, i.e. "left" of −104 ppm). Further, an increase of signal at the right hand side of the spectrum (here: below −110 ppm, i.e. "right" of −110 ppm) was observed, which region comprises $Q^4$ structures exclusively. For the quantification of spectrum changes, a ratio was calculated that reflects changes in the peak areas "left hand" and "right hand", as follows. The six peaks were labeled with 1, 2, 3, 4, 5, and 6, and the ratio Q was calculated with the formula 100*{$[a_1+a_2]/[a_4+a_5+a_6]$}/$a_3$. In this formula, $a_{i,\ i=1\ \ldots\ 6}$ represents the area of the fitted peak to which this number was attributed.

Reference Example 2.5: Water Adsorption/Desorption—Water Uptake

The water adsorption/desorption isotherms measurements were performed on a VTI SA instrument from TA Instruments following a step-isotherm program. The experiment consisted of a run or a series of runs performed on a sample material that has been placed on the microbalance pan inside of the instrument. Before the measurement were started, the residual moisture of the sample was removed by heating the sample to 100° C. (heating ramp of 5° C./min) and holding it for 6 h under a $N_2$ flow. After the drying program, the temperature in the cell was decreased to 25° C. and kept isothermal during the measurements. The microbalance was calibrated, and the weight of the dried sample was balanced (maximum mass deviation 0.01 weight-%). Water uptake by the sample was measured as the increase in weight over that of the dry sample. First, an adsorption curve was measured by increasing the relative humidity (RH) (expressed as weight-% water in the atmosphere inside of the cell) to which the samples was exposed and measuring the water uptake by the sample at equilibrium. The RH was increased with a step of 10 weight-% from 5 to 85% and at each step the system controlled the RH and monitored the sample weight until reaching the equilibrium conditions and recording the weight uptake. The total adsorbed water amount by the sample was taken after the sample was exposed to the 85 weight-% RH. During the desorption measurement the RH was decreased from 85 weight-% to 5 weight-% with a step of 10% and the change in the weight of the sample (water uptake) was monitored and recorded.

Reference Example 2.6: FT-IR Measurements

The FT-IR (Fourier-Transformed-Infrared) measurements were performed on a Nicolet 6700 spectrometer. The molding was powdered and then pressed into a self-supporting pellet without the use of any additives. The pellet was introduced into a high vacuum (HV) cell placed into the FT-IR instrument. Prior to the measurement the sample was pretreated in high vacuum ($10^{-5}$ mbar) for 3 h at 300° C. The spectra were collected after cooling the cell to 50° C. The spectra were recorded in the range of 4000 to 800 $cm^{-1}$ at a resolution of 2 $cm^{-1}$. The obtained spectra are represented in a plot having on the x axis the wavenumber ($cm^{-1}$) and on the y axis the absorbance (arbitrary units, a.u.). For the quantitative determination of the peak heights and the ratio between these peaks a baseline correction was carried out. Changes in the 3000-3900 $cm^{-1}$ region were analyzed and for comparing multiple samples, as reference the band at 1880±5 $cm^{-1}$ was taken.

Reference Example 2.7: Determination of Crystallinity Via XRD

The crystallinity of the zeolitic materials according to the present invention were determined by XRD analysis. The data were collected using a standard Bragg-Brentano diffractometer with a Cu-X-ray source and an energy dispersive point detector. The angular range of 2° to 70° (2 theta) was scanned with a step size of 0.02°, while the variable divergence slit was set to a constant illuminated sample length of 20 mm. The data were then analyzed using TOPAS V4 software, wherein the sharp diffraction peaks were modeled using a Pawley fit containing a unit cell with the following starting parameters: a=14.4 Angstrom (1 Angstrom=$10^{-10}$ m) and c=25.2 Angstrom in the space group P6/mmm. These were refined to fit the data. Independent peaks were inserted at the following positions. 8.4°, 22.4°, 28.2° and 43°. These were used to describe the amorphous content. The crystalline content describes the intensity of the crystalline signal to the total scattered intensity. Included in the model were also a linear background, Lorentz and polarization corrections, lattice parameters, space group and crystallite size.

Reference Example 3: Epoxidation Process

A main reactor A was a vertically mounted tube-bundle reactor with 5 tubes (length of the tubes: 12 m, internal tube diameter: 38 mm), each tube being equipped with an axially placed multipoint thermocouple with 10 equally spaced measuring points encased in a suitable thermowell with a diameter of 18 mm. Each tube was charged with 17.5 kg of the ZnTiMWW catalyst moldings as prepared according to Reference Example 1 (post-treated moldings). Free space eventually remaining was filled with steatite spheres (diameter of 3 mm). The heat of reaction was removed by circulating a thermostatized heat transfer medium (water/glycol mixture) on the shell side in co-current direction to the feed. The flow rate of the heat transfer medium was adjusted so that the temperature difference between entrance and exit did not exceed 1° C. The reaction temperature referred to hereinbelow, also referred to as TR, was defined as the temperature of the heat transfer medium entering the reactor shell. At the reactor exit, the pressure was controlled by a pressure regulator and kept constant at 20 bar(abs). The output stream (5) leaving the epoxidation unit A was sampled every 20 minutes in order to determine the hydrogen peroxide concentration using the titanyl sulfate method and to calculate the hydrogen peroxide conversion. The hydrogen peroxide conversion was defined as $100 \times (1-m_{out}/m_{in})$ wherein $m_{in}$ is the molar flow rate of $H_2O_2$ in the reactor feed and $m_{out}$ is the molar flow rate of $H_2O_2$ in the reactor outlet. Based on the respectively obtained hydrogen peroxide conversion values, the inlet temperature of the heat transfer medium was adjusted in order to keep the hydrogen peroxide conversion essentially constant in the range of from 90 to 92%. The inlet temperature of the heat transfer medium was set at 30° C. at the start of a given run with a fresh batch of the epoxidation catalyst and was increased, if necessary, to maintain the hydrogen peroxide conversion in the mentioned range. The required temperature increase was usually less than 1 K/d. The output stream (5) leaving the epoxidation unit A was passed through a heat exchanging unit. The stream leaving the heat exchanging unit (stream S) was fed to Epoxidation Unit B.

Epoxidation in a Finishing Reactor (Epoxidation Unit B): The finishing reactor B was a fixed bed reactor operated adiabatically. In this context, the term "adiabatic" refers to an operation mode according to which no active cooling is carried out and according to which the finishing reactor is suitably insulated in order to minimize heat losses. The finishing reactor B had a length of 4 m and a diameter of 100 mm. The reactor was filled with 9 kg of the same epoxidation catalyst which was used in the main epoxidation reactor A. Spare space was filled with steatite spheres (diameter of 3 mm). The operating pressure of the finishing reactor B was 10 bar which was kept constant by a suitable pressure regulator at the reactor exit. The output of the finishing reactor B was sampled every 20 min in order to determine the hydrogen peroxide concentration using the titanyl sulfate method. The effluent of the finishing reactor B, stream (6), was preferably depressurized into a flash drum, and both the liquid and the gas from this drum were fed to a light boiler separation column (distillation unit C).

The main reactor A was fed from below with a liquid monophasic stream (1). Stream (1) was prepared by mixing five streams (2), (2a), (3), (4) and (5). The temperature of stream (1) was in the range from 20 to 40° C. The streams were premixed at an absolute pressure of 23 bar. The liquid feed stream (1) consisted of one single liquid phase:

Stream (2) was an acetonitrile stream and had a flow rate of 69 kg/h.

Stream (2a) was a water stream and had a flow rate of 3 kg/h.

Stream (3) having a flow rate of 12.9 kg/h was a propylene stream (containing 0.35 kg/h propene) and was supplied from a storage tank, allowing for a continuous feeding, and fed using a suitable metering pump.

Stream (4) having a flow rate of 15 kg/h was an aqueous hydrogen peroxide solution having a hydrogen peroxide concentration of 40 weight-% ("crude/washed" grade from Solvay with a TOC in the range of 100 to 400 mg/kg). The aqueous hydrogen peroxide solution was supplied from a storage tank, allowing for a continuous feeding, and fed using a suitable metering pump.

Stream (5) was an aqueous stream comprising dissolved potassium formate. The further stream was supplied from a storage tank, allowing for a continuous feeding, and was fed using a suitable metering pump. The concentration of the potassium formate was 2.5 weight-%, the feed rate of the stream was 500 g/h (1000 μmol potassium/mol hydrogen peroxide). Stream (5) was thoroughly mixed with stream (4) before the combined stream was mixed with the stream resulting from mixing streams (2), 2a) and (3).

The epoxidation was performed in a continuous manner.

The reactor effluent stream downstream the pressure control valve was collected, weighed and analyzed (effluent stream (6)). Organic components, with the exception of oxygen, were analyzed in two separate gas-chromatographs. The hydrogen peroxide content was determined colorimetrically using the titanyl sulfate method. Effluent stream (6) comprised 66.5 weight-% acetonitrile, 17.4 weight-% water, 11.6 weight-% propylene oxide, 3.8 weight-% propylene, 0.13 weight-% propylene glycol, 0.5 weight-% propane, 0.03 weight-% oxygen, 0.02 weight-% acetaldehyde, 0.01 weight-% propionaldehyde.

Reference Example 4: Separation of Propylene from Stream (6) to Obtain Stream S0

Separation of Light Boilers from Stream (6) to Obtain a Stream (8) (Stream S0)

Stream (6) was sent to a light boiler separation column (distillation unit C) operated at 1.1 bar. The distillation column had a length of 8.5 m, a diameter of 170 mm, and was equipped with 40 bubble trays, an evaporator at the bottom and a condenser at the top. The column was operated as a mixed washing/distillation tower. As a washing agent, part of the bottoms stream of distillation unit D (stream 11, about 20-30 kg/h) was taken off, cooled to 10° C. and introduced at the top of the column. Liquid and gaseous inlet streams were introduced to the column at different points. The feed point of the liquid portion of stream (6) was above bubble tray 37; the gaseous portion of stream (6) was introduced into the column above bubble tray 28 (counted from the top). The gaseous stream (7) leaving the cooling means at the top of the column contained mainly propene, propane (which was contained as impurity in the polymer-grade propene used), oxygen formed as a by-product and small amounts of other light boilers (acetonitrile (1-2 volume-%), propionaldehyde (about 200 volume-ppm), acetone (about 100 volume-ppm, $H_2$ (about 400 volume-ppm), $CO_2$ (about 400 volume-ppm) and acetaldehyde (about 100 volume-ppm)), and was essentially free of propylene oxide (less than 300 volume-ppm). This top stream was sent to the flare for disposal. Stream (8) (that is stream S0) was taken off of the light boiler separation column as bottoms stream.

Reference Example 5: Determination of Conditions and Product Compositions in Propylene Oxide Separation

Reference Example 5.1: Determination of Number of Theoretical Trays

The number of theoretical trays was determined according to known methods with a test mixture of chlorobenzene and ethyl benzene at a top pressure of 500 mbar (absolute).

Reference Example 5.2: Gaschromatography

The composition of the organic products was determined by calibrated GC method. The detection limit was estimated to be 1 weight-ppm. The fault of the gas chromatographically concentration measurements was estimated to be ±1% in the weight-% area and ±5% in the ppm area.
GC 6890 auto sampler 7693, column stabilwax, 60 m×0.32 mm×1 μm, FID
Injector
Temperature: 200° C.
Splitting ratio: 33.2:1
Injection volume: 1 μl
Constant pressure of 0.6 bar
Carrier gas: nitrogen
Oven Program
40° C./5 min//2° C.min-1/120° C./0 min//
Detector
Temperature 250° C., hydrogen 40 l/min, oxygen 400 l/min
Calibration
Internal standard (dioxane) 10%

Reference Example 5.3: Determination of Water Content

The water content in top products and products taken off from the sump of a column was determined by volumetric Karl-Fischer-titration (working medium K) in dry methanol. The sump water content was indirectly determined (as 100 minus the sum of the contents of all other components).

Reference Example 5.4: Determination of Mass Flows

The fault in measuring the mass flows using mass flow meters (Ultrasonic in-line flow meter; SensoTech 40-14) was estimated to be ±2%.

Example 1: Separating Propylene Oxide from the Stream S0

A continuous glass distillation column equipped with a high-performance packing (high performance packing Sulzer CY) was used. The total packing height was 8.1 m, which equaled to 130 theoretical trays, with a packing of 3.6 m below the S0 feed point, 0.9 m packing between feed and side take-off and 3.6 m packing above the side take-off (counted from the bottom). The pressure at the top of the column was automatically regulated and kept constant at 500 mbar (absolute).
The feed stream (stream S0) composition was indicated in Table 1.

TABLE 1

| composition of stream S0 in Example 1 | |
|---|---|
| Component | content |
| acetonitrile | 70.7 weight-% |
| water | 18.9 weight-% |
| Propylene oxide | 10.1 weight-% |
| propionaldehyde | 196 weight-ppm |
| acetaldehyde | 145 weight-ppm |
| acetone | 102 weight-ppm |
| Propylene glycol | 0.21 weight-% |

Stream S0 was introduced into the column with a rate of 2.0 kg/h and a temperature of 41.4° C.
The amount of stream S0, the amount of side take off stream S1b and the amount of the reflux were kept constant by flow controller. The amount of top stream S1c was taken off from the distillate container under level control. In order to regulate the energy supply to the sump, the average value of two temperature measuring points positioned between feed and side take off was taken as guidance value and was kept constant. The temperature of the oil used for heating the sump boiler was used as variable.
The distillation was kept running until all compositions were stationary, especially the composition within the side take off stream S1b. Thereafter, balancing was done over 6 hours.
The amount of reflux was kept constant at 800 g/h resulting in an average reflux ratio of 4. Stream S1c was taken off at the top of the column with 200 g/h, sump stream S1a was taken off with an average of 1797 g/h and side take off stream S1b was taken off as a constant stream with 3 g/h. The compositions of streams S1a, S1b and S1c were indicated in Table 2.

TABLE 2

| composition of streams S1a, S1b and S1c of Example 1 | | | |
|---|---|---|---|
| | Sump stream S1a | Side take off stream S1b | Top stream S1c |
| acetonitrile | 76.9 weight-% | 4.3 weight-% | <1 weight-ppm |
| water | 22.8 weight-% | 3.3 weight-% | 37.0 weight-ppm |
| propylene oxide | <1 weight-ppm | 71.0 weight-% | 99.9 weight-% |
| propionaldehyde | <1 weight-ppm | 14.7 weight-% | 11 weight-ppm |
| acetaldehyde | <1 weight-ppm | 92 weight-ppm | 0.13 weight-% |
| acetone | <1 weight-ppm | 6.8 weight-% | 2.0 weight-ppm |
| propylene glycol | 0.3 weight-% | 14 weight-ppm | <1 weight-ppm |

The resulting temperatures within the column were: Top (16.0° C.) and sump (56.8° C.). In order to regulate the oil temperature for the sump boiler, 39° C. was chosen as target value of the temperature average value of the two temperature measure points between feed and side take off.
It could be observed that these conditions resulted in a propylene oxide top stream from one single column containing less than 50 weight-ppm water and less than 30 weight-ppm propionaldehyde. The top stream also contained less than 5 weight-ppm acetone. Further, almost the whole amount of acetone and propionaldehyde could be separated via the side take off, i.e. both top stream and sump stream were essentially free of propionaldehyde and acetone. Acetalhdeyde, which was still contained in the top stream, was easily separable in a later separations stage. The loss on propylene oxide via the side take off stream S1b was low (1 weight-% of the complete amount).

Comparative Example 2: Separation of Propylene Oxide from Stream S0 Using a Shorter Column A continuous glass distillation column equipped with a high-performance packing (high performance packing Sulzer CY) was used. The total packing height was 6.3 m, which equaled to 100 theoretical trays, with a packing of 2.8 m below the S0 feed point, 0.7 m packing between feed and side take-off and 2.8 m packing above the side take-off (counted from the bottom). The pressure at the top of the column was automatically regulated and kept constant at 500 mbar (absolute). Table 3 showed the composition of feed stream S0, which was identical to that of S0 in Example 1.

TABLE 3 composition of stream S0 in Comparative Example 2

| Component | content |
| --- | --- |
| acetonitrile | 70.7 weight-% |
| water | 18.9 weight-% |
| Propylene oxide | 10.1 weight-% |
| propionaldehyde | 196 weight-ppm |
| acetaldehyde | 145 weight-ppm |
| acetone | 102 weight-ppm |
| Propylene glycol | 0.21 weight-% |

Feed stream S0 was introduced into the column with a rate of 2.0 kg/h and a temperature of 41.4° C. as done in Example 1.

The column was regulated identically as described in Example 1.

The distillation was kept running until all compositions were stationary, especially the composition within the side take off stream S1b. Thereafter, balancing was done over 6 hours.

The amount of reflux was kept constant at 1400 g/h resulting in an average reflux ratio of 6.3. Stream S1c was taken off at the top of the column with in average 221 g/h, sump stream S1a was taken off with an average of 1777 g/h and side take off stream S1b was taken off as a constant stream with 2 g/h. The compositions of streams S1a, S1 b and S1c were indicated in Table 4.

TABLE 4 composition of streams S1a, S1b and S1c of Comparative Example 2

| | Sump stream S1a | Side take off stream S1b | Top stream S1c |
| --- | --- | --- | --- |
| acetonitrile | 77.5 weight-% | 6.7 weight-% | 60 weight-ppm |
| water | 22.2 weight-% | 3.6 weight-% | 400 weight-ppm |
| propylene oxide | <1 weight-ppm | 64.6 weight-% | 99.8 weight-% |
| propion-aldehyde | 20 weight-ppm | 20.0 weight-ppm | 20 weight-ppm |
| acetaldehyde | <1 weight-ppm | 170 weight-ppm | 0.14 weight-% |
| acetone | 57 weight-ppm | 5.0 weight-% | 50 weight-ppm |
| propylene glycol | 0.23 weight-% | 14 weight-ppm | <1 weight-ppm |

The resulting temperatures within the column were: Top (16.0° C.) and sump (56.8° C.), which were identical to those of Example 1. In order to regulate the oil temperature for the sump boiler, 39° C. was chosen as target value of the temperature average value of the two temperature measure points between feed and side take off, as done in Example 1.

It could be observed that these conditions even with a number of theoretical trays of 100, despite a higher reflux ratio, resulted in a propylene oxide top stream containing significantly more than 50 weight-ppm water (400 weight-ppm) even if low amounts of propionaldehyde could be achieved (20 weight-ppm) in said top stream. Further, the sump stream still contained measurable amounts of propionaldehyde and acetone.

SHORT DESCRIPTION OF THE FIGURE

FIG. 1 shows a block diagram of the process according to Reference Examples 3, 4 and Example 1. In FIG. 1, the letters and numbers have the following meanings:

| | |
| --- | --- |
| A | epoxidation unit A |
| B | epoxidation unit B |
| C | distillation unit |
| D | distillation unit |
| (1), (5), (6), (7), (8) | streams according to a preferred process as described in the Reference Examples 3, 4 and in Example 1 |
| S0, S1a, S1b, S1c | streams according to a specifically preferred process as described in the general description and in Example 1 |

CITED LITERATURE

U.S. Pat. No. 5,133,839 A
U.S. Pat. No. 5,489,366 A
JP 44009650 A
U.S. Pat. No. 4,369,096 A
WO 2004/048355 A
EP 2 173 731 A2
EP 1 122 249 A1
Ullmann's Encyclopedia of Industrial Chemistry, 5$^{th}$ edition, volume A 13 (1989) pages 443-466

The invention claimed is:

1. A process for purifying propylene oxide, the process comprising:
  (i) providing a stream S0 comprising propylene oxide, acetonitrile, water, and comprising at least one of acetone and propionaldehyde; and
  (ii) separating propylene oxide from the stream S0 by distillation, comprising subjecting the stream S0 to distillation conditions in a distillation column, obtaining a gaseous top stream S1c which is enriched in propylene oxide compared to the stream S0, a liquid bottoms stream S1a which is enriched in acetonitrile and water compared to the stream S0, and a side stream S1b comprising propylene oxide which is enriched in at least one of acetone and propionaldehyde compared to the stream S0;
  wherein:
  the distillation column is operated at an absolute pressure at the top of the distillation column in the range of from 0.1 to 2.0 bar and an internal reflux ratio in the range of from 2.0 to 6.0; and
  the distillation column exhibits at least 100 theoretical trays, a rectifying section of the distillation column consists of from 30 to 70% of the theoretical trays and a stripping section of the distillation column consists of from 70 to 30% of the theoretical trays.

2. The process of claim 1, wherein the distillation column is operated at an absolute pressure at the top of the distillation column in the range of from 0.2 to 1.5 bar.

3. The process of claim 1, wherein the distillation column is operated at a reflux ratio in the range of from 2.5 to 5.5.

4. The process of claim 1, wherein the distillation column exhibits from 100 to 150 theoretical trays.

5. The process of claim 1, wherein the side stream S1b is removed from the rectifying section of the distillation column.

6. The process of claim 1, wherein the side stream S1b is removed from the rectifying section of the distillation column at a position which is at least 1 theoretical tray above the stripping section of the distillation column.

7. The process of claim 1, wherein the side stream S1b is removed from the rectifying section of the distillation column at a position which is from 1 to 20 theoretical tray above the stripping section of the distillation column.

8. The process of claim 1, wherein the stream S0 further comprises at least one of an aldehyde and a ketone.

9. The process of claim 1, wherein the stream S0 further comprises at least one selected from the group consisting of acetaldehyde, formaldehyde, butyraldehyde, isobutyraldehyde, 2-butanon, 1-pentanal, 2-pentanon, 3-pentanon, and 2-methylpentanone.

10. The process of claim 1, wherein the stream S0 is obtained by a process comprising:
(a) providing a liquid feed stream comprising propene and optionally propane, hydrogen peroxide or a source of hydrogen peroxide, water, and acetonitrile;
(b) passing the liquid feed stream into an epoxidation zone comprising an epoxidation catalyst comprising a titanium zeolite, and subjecting the liquid feed stream to epoxidation reaction conditions in the epoxidation zone, obtaining a reaction mixture comprising propene and optionally propane, propylene oxide, water, acetonitrile, and at least one of acetone and propionaldehyde;
(c) removing an effluent stream from the epoxidation zone, the effluent stream comprising propylene oxide, water, acetonitrile, propene and optionally propane, and at least one of acetone and propionaldehyde; and
(d) separating propene and optionally propane from the effluent stream by distillation, comprising subjecting the effluent stream to distillation conditions in a distillation unit, obtaining a gaseous stream which is enriched in propene and optionally propane compared to the effluent stream subjected to distillation conditions, and a liquid bottoms stream which is enriched in propylene oxide, water, acetonitrile and at least one of acetone and propionaldehyde compared to the effluent stream subjected to distillation conditions;
wherein said liquid bottoms stream obtained according to (d) is the stream S0.

11. The process of claim 1, wherein providing the stream S0 according to (i) comprises:
(a) providing a liquid feed stream comprising propene and optionally propane, hydrogen peroxide or a source of hydrogen peroxide, water, and acetonitrile;
(b) passing the liquid feed stream provided in (a) into an epoxidation zone comprising an epoxidation catalyst comprising a titanium zeolite, and subjecting the liquid feed stream to epoxidation reaction conditions in the epoxidation zone, obtaining a reaction mixture comprising propene and optionally propane, propylene oxide, water, acetonitrile, and at least one of acetone and propionaldehyde;
(c) removing an effluent stream from the epoxidation zone, the effluent stream comprising propylene oxide, water, acetonitrile, propene and optionally propane, and at least one of acetone and propionaldehyde;
(d) separating propene and optionally propane from the effluent stream by distillation, comprising subjecting the effluent stream to distillation conditions in a distillation unit, obtaining a gaseous stream which is enriched in propene and optionally propane compared to the effluent stream subjected to distillation conditions, and a liquid bottoms stream which is enriched in propylene oxide, water, acetonitrile and at least one of acetone and propionaldehyde compared to the effluent stream subjected to distillation conditions;
wherein said liquid bottoms stream obtained according to (d) is the stream S0.

12. The process of claim 1, wherein the top stream S1c obtained in (ii) contains at least 99.00 weight propylene oxide based on the total weight of the stream S1c.

13. The process of claim 1, wherein the top stream S1c obtained in (ii) contains at the outmost 50 weight-ppm of at least one of acetone and propionaldehyde based on the total weight of the stream S1c.

14. The process of claim 1, wherein the top stream S1c obtained in (ii) contains at the outmost 100 weight-ppm water based on the total weight of the stream S1c.

15. The process of claim 1, wherein bottoms stream S1a contains at least one of acetone and propionaldehyde in an amount of at most 20 weight-ppm based on the weight of S1a.

16. The process of claim 1, wherein at least 95 weight-% of bottoms stream S1a consist of acetonitrile and water.

17. The process of claim 1, wherein bottoms stream S1a contains at most 10 weight-ppm of the propylene oxide, based on the weight of S1a.

18. The process of claim 1, wherein:
the side stream S1b comprises at least one of acetone and propionaldehyde in an amount of ≥10 weight-%, based on the total weight of the side stream S1b; and
the at least one of acetone and propionaldehyde optionally comprises propionaldehyde in an amount of ≥10 weight-% based on the total weight of the side stream S1b and acetone in an amount of ≥5 weight-% based on the total weight of the side stream S1b.

19. The process of claim 1, wherein at least 95 weight-% of the side stream S1b consist of propylene oxide, acetonitrile, water, and at least one of acetone and propionaldehyde.

20. The process of claim 1, which is a continuous process.

* * * * *

UNITED STATES PATENT AND TRADEMARK OFFICE
CERTIFICATE OF CORRECTION

PATENT NO. : 10,544,116 B2
APPLICATION NO. : 16/315680
DATED : January 28, 2020
INVENTOR(S) : Joaquim Henrique Teles et al.

It is certified that error appears in the above-identified patent and that said Letters Patent is hereby corrected as shown below:

In the Specification

In Column 1, Line 44, delete "destillative" and insert -- distillative --, therefor.

In Column 2, Line 4, delete "destillative" and insert -- distillative --, therefor.

In Column 3, Line 65, delete "ore" and insert -- or --, therefor.

In Column 4, Line 54, delete "S1 b;" and insert -- S1b; --, therefor.

In Column 4, Line 59, delete "S1 b." and insert -- S1b. --, therefor.

In Column 4, Line 67, delete "S1 b;" and insert -- S1b; --, therefor.

In Column 5, Line 2, delete "S1 b;" and insert -- S1b; --, therefor.

In Column 5, Line 5, delete "S1 b;" and insert -- S1b; --, therefor.

In Column 5, Line 9, delete "S1 b," and insert -- S1b, --, therefor.

In Column 5, Line 11, delete "S1 b." and insert -- S1b. --, therefor.

In Column 5, Line 28, delete "ore" and insert -- or --, therefor.

In Column 7, Line 56, delete "and and" and insert -- and --, therefor.

In Column 13, Line 65, delete "ore" and insert -- or --, therefor.

In Column 17, Line 2, delete "S1 b;" and insert -- S1b; --, therefor.

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,544,116 B2

In Column 17, Line 4, delete "10" and insert -- ≥10 --, therefor.

In Column 17, Line 6, before "weight-%" insert -- ≥5 --.

In Column 17, Line 17, delete "S1 b;" and insert -- S1b; --, therefor.

In Column 17, Line 19, delete "S1 b;" and insert -- S1b; --, therefor.

In Column 17, Line 27, delete "S1 b," and insert -- S1b, --, therefor.

In Column 17, Line 29, delete "S1 b." and insert -- S1b. --, therefor.

In Column 20, Line 4, delete "g/I" and insert -- g/l --, therefor.

In Column 20, Line 55, delete "g/I" and insert -- g/l --, therefor.

In Column 21, Line 9, delete "mulitpoint" and insert -- multipoint --, therefor.

In Column 21, Line 21, delete "deioinized" and insert -- deionized --, therefor.

In Column 21, Line 36, delete "g/I" and insert -- g/l --, therefor.

In Column 21, Line 62, delete "t" and insert -- to --, therefor.

In Column 26, Line 60, delete "(1-2" and insert -- 1-2 --, therefor.

In Column 26, Line 62, delete "ppm," and insert -- ppm), --, therefor.

In Column 26, Line 64, delete "ppm))," and insert -- ppm), --, therefor.

In Column 27, Line 12, delete "Gaschromatography" and insert -- Gas chromatography --, therefor.

In Column 28, Line 66, delete "Acetalhdeyde," and insert -- Acetaldehyde, --, therefor.